(12) United States Patent
Morrison et al.

(10) Patent No.: US 8,119,788 B2
(45) Date of Patent: Feb. 21, 2012

(54) **COMPOSITIONS AND METHODS FOR THE DETECTION OF *CANDIDA* SPECIES**

(75) Inventors: Christine J. Morrison, Decatur, GA (US); Sanchita Das, New York, NY (US); Teresa Brown, Lawrenceville, GA (US); Brian Holloway, Atlanta, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 615 days.

(21) Appl. No.: 12/088,235

(22) PCT Filed: Sep. 26, 2006

(86) PCT No.: PCT/US2006/037640
§ 371 (c)(1),
(2), (4) Date: Mar. 26, 2008

(87) PCT Pub. No.: WO2007/038578
PCT Pub. Date: Apr. 5, 2007

(65) Prior Publication Data
US 2008/0248970 A1    Oct. 9, 2008

Related U.S. Application Data

(60) Provisional application No. 60/721,419, filed on Sep. 27, 2005.

(51) Int. Cl.
*C40B 40/06*    (2006.01)

(52) U.S. Cl. .................. 536/24.32; 536/23.1; 506/16
(58) Field of Classification Search .................. None
See application file for complete search history.

(56) References Cited

U.S. PATENT DOCUMENTS

| | | |
|---|---|---|
| 5,284,747 A | 2/1994 | Milliman |
| 5,302,527 A * | 4/1994 | Birkett et al. .............. 435/254.5 |
| 5,352,579 A | 10/1994 | Milliman |
| 5,426,027 A | 6/1995 | Lott et al. |

(Continued)

FOREIGN PATENT DOCUMENTS
WO    WO/9624691    8/1996

(Continued)

OTHER PUBLICATIONS

Das et al., "DNA probes for the rapid identification of medically important *Candida* species using a multianalyte profiling system," *FEMS Immunology and Medical Microbiology*, 2006, 46(2): 244-250.

(Continued)

*Primary Examiner* — Albert Navarro
*Assistant Examiner* — Ginny Portner
(74) *Attorney, Agent, or Firm* — Klarquist Sparkman, LLP

(57) ABSTRACT

Compositions and methods for detecting and/or differentiating among *Candida* organisms, including *C. albicans* and *C. dubliniensis*, are disclosed. Exemplary methods involve screening a sample suspected of containing at least one or more *Candida* sp. for the presence or absence of a nucleic acid sequence specific for each such fungal pathogen. Some disclosed methods permit the rapid and simultaneous detection and identification of several fungal pathogens (e.g., up to 100 fungi) in a single sample.

15 Claims, 3 Drawing Sheets

U.S. PATENT DOCUMENTS

| | | | |
|---|---|---|---|
| 5,501,951 | A | 3/1996 | Milliman |
| 5,558,990 | A | 9/1996 | Milliman |
| 5,622,827 | A | 4/1997 | McAllister et al. |
| 5,631,132 | A | 5/1997 | Lott et al. |
| 5,635,353 | A | 6/1997 | Lott et al. |
| 5,645,992 | A | 7/1997 | Lott et al. |
| 5,688,644 | A | 11/1997 | Lott et al. |
| 5,693,501 | A | 12/1997 | Lee et al. |
| 5,707,802 | A | 1/1998 | Sandhu et al. |
| 5,763,169 | A | 6/1998 | Sandhu et al. |
| 6,180,339 | B1 | 1/2001 | Sandhu et al. |
| 6,235,890 | B1 * | 5/2001 | Morrison et al. ......... 536/24.33 |
| 6,242,178 | B1 * | 6/2001 | Lott et al. ......................... 435/6 |
| 6,469,156 | B1 | 10/2002 | Schafer et al. |
| 2004/0185453 | A1 * | 9/2004 | Myerson et al. ................. 435/6 |
| 2004/0248090 | A1 * | 12/2004 | Olek et al. ....................... 435/6 |
| 2005/0065330 | A1 | 3/2005 | Procop |
| 2008/0102449 | A1 * | 5/2008 | Trama et al. ..................... 435/6 |

FOREIGN PATENT DOCUMENTS

| | | | |
|---|---|---|---|
| WO | 98/11257 | * | 3/1998 |
| WO | WO 99/06596 | | 2/1999 |
| WO | WO/9954508 | | 10/1999 |
| WO | 01/42493 | * | 6/2001 |

OTHER PUBLICATIONS

Elie et al., "Rapid Identification of *Candida* Species with Species-Specific DNA Probes," *Journal of Clinical Microbiology*, Nov.1998, 36(11): 3260-3265.

Ellepola et al., "Rapid and unequivocal differentiation of *Candida dubliniensis* from other *Candida* species using species-specific DNA probes: Comparison with phenotypic identification methods," *Oral Microbiology and Immunology*, 2003, 18(6): 379-388.

Ellepola and Morrison, "Laboratory Diagnosis of Invasive Candidiasis," *The Journal of Microbiology*, Feb. 2005, 43(S): 66-84.

Fujita et al., "Microtitration Plate Enzyme Immunoassay to Detect PCR-Amplified DNA from *Candida* Species in Blood," *Journal of Clinical Microbiology*, Apr. 1995, 33(4): 962-967.

International Search Report dated Sep. 26, 2006, issued in International Application No. PCT/US2006/037640, 5 pages.

Lindsley et al., "Rapid Identification of Dimorphic and Yeast-Like Fungal Pathogens Using Specific DNA Probes," *Journal of Clinical Microbiology*, Oct. 2001, 39(10): 3505-3511.

Shin et al., "Rapid Identification of *Candida* Species in Blood Cultures by a Clinically Useful PCR Method," *Journal of Clinical Microbiology*, Jun. 1997, 35(6): 1454-1459.

Shin et al., "Rapid Identification of up to Three *Candida* Species in a Single Reaction Tube by a 5' Exonuclease Assay Using Fluorescent DNA Probes," *Journal of Clinical Microbiology*, Jan. 1999, 37(1): 165-170.

Coignard et al., "Resolution of Discrepant Results for *Candida* Species Identification by Using DNA Probes," *Journal of Clinical Microbiology*, vol. 42, No. 2, pp. 858-861, 2004.

Diaz and Fell, "High-Throughput Detection of Pathogenic Yeasts of the Genus *Trichosporon*," *Journal of Clinical Microbiology*, vol. 42, No. 8, pp. 3696-3706, 2004.

Huffnagle et al., "Evaluation of Gen-Probe' s *Histoplasma capsulatum* and *Cryptococcus neoformans* AccuProbes," *Journal of Clinical Microbiology*, vol. 31, No. 2, pp. 419-421, 1993.

Keath et al., "DNA Probe for the Identification of *Histoplasma capsulatum*," *Journal of Clinical Microbiology*, vol. 27, No. 10, pp. 2369-2372, 1989.

Padhye et al., "Comparative Evaluation of Chemiluminescent DNA Probe Assays and Exoantigen Tests for Rapid Identification of *Blastomyces dermatitidis* and *Coccidioides immitits*," *Journal of Clinical Microbiology*, vol. 32, No. 4, pp. 867-870, 1994.

* cited by examiner

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: CA2 nucleic acid probe

```
<400> SEQUENCE: 1
attgcttgcg gcggtaacgt                                                    20

<210> SEQ ID NO 2
<211> LENGTH: 21
<212> TYPE: DNA
<213> ORGANISM: Artificial Sequence
<220> FEATURE:
<223> OTHER INFORMATION: CD2 nucleic acid probe

<400> SEQUENCE: 2
aaggcggtct ctggcgtcgc c                                                  21

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gcatcgatga agaacgcagc                                                    20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tcctccgctt attgatatgc                                                    20

<210> SEQ ID NO 5
<211> LENGTH: 22
<212> TYPE: DNA
<213> ORGANISM: Artificial Sequence
<220> FEATURE:
<223> OTHER INFORMATION: CA1 nucleic acid probe

<400> SEQUENCE: 5
attgcttgcg gcggtaacgt cc                                                 22

<210> SEQ ID NO 6
<211> LENGTH: 22
<212> TYPE: DNA
<213> ORGANISM: Artificial Sequence
<220> FEATURE:
<223> OTHER INFORMATION: CD1 nucleic acid probe

<400> SEQUENCE: 6
aaggcggtct ctggcgtcgc cc                                                 22

<210> SEQ ID NO 7
<211> LENGTH: 22
<212> TYPE: DNA
<213> ORGANISM: Artificial Sequence
<220> FEATURE:
<223> OTHER INFORMATION: CG nucleic acid probe

<400> SEQUENCE: 7
taggttttac caactcggtg tt                                                 22
```

```
<210> SEQ ID NO 8
<211> LENGTH: 22
<212> TYPE: DNA
<213> ORGANISM: Artificial Sequence
<220> FEATURE:
<223> OTHER INFORMATION: CGE nucleic acid probe

<400> SEQUENCE: 8
tttaccaact cggtgttgat ct                                              22

<210> SEQ ID NO 9
<211> LENGTH: 22
<212> TYPE: DNA
<213> ORGANISM: Artificial Sequence
<220> FEATURE:
<223> OTHER INFORMATION: GU nucleic acid probe

<400> SEQUENCE: 9
cccggcctta caacaaccaa ac                                              22

<210> SEQ ID NO 10
<211> LENGTH: 22
<212> TYPE: DNA
<213> ORGANISM: Artificial Sequence
<220> FEATURE:
<223> OTHER INFORMATION: CH nucleic acid probe

<400> SEQUENCE: 10
ccgttggtgg atttgtttct aa                                              22

<210> SEQ ID NO 11
<211> LENGTH: 22
<212> TYPE: DNA
<213> ORGANISM: Artificial Sequence
<220> FEATURE:
<223> OTHER INFORMATION: KF nucleic acid probe

<400> SEQUENCE: 11
gagactcata ggtgtcataa ag                                              22

<210> SEQ ID NO 12
<211> LENGTH: 22
<212> TYPE: DNA
<213> ORGANISM: Artificial Sequence
<220> FEATURE:
<223> OTHER INFORMATION: CK nucleic acid probe

<400> SEQUENCE: 12
ggcccgagcg aactagactt tt                                              22

<210> SEQ ID NO 13
<211> LENGTH: 22
<212> TYPE: DNA
<213> ORGANISM: Artificial Sequence
<220> FEATURE:
<223> OTHER INFORMATION: LA2 nucleic acid probe

<400> SEQUENCE: 13
aaagcgaggg gccttctgcg cg                                              22

<210> SEQ ID NO 14
<211> LENGTH: 22
<212> TYPE: DNA
<213> ORGANISM: Artificial Sequence
<220> FEATURE:
<223> OTHER INFORMATION: LA4 nucleic acid probe
```

```
<400> SEQUENCE: 14
gcgaggggcc ttctgcgcga ac                                              22

<210> SEQ ID NO 15
<211> LENGTH: 22
<212> TYPE: DNA
<213> ORGANISM: Artificial Sequence
<220> FEATURE:
<223> OTHER INFORMATION: LU nucleic acid probe

<400> SEQUENCE: 15
ctccgaaata tcaaccgcgc tg                                              22

<210> SEQ ID NO 16
<211> LENGTH: 22
<212> TYPE: DNA
<213> ORGANISM: Artificial Sequence
<220> FEATURE:
<223> OTHER INFORMATION: NS nucleic acid probe

<400> SEQUENCE: 16
actgagcgaa gtacacaaca ct                                              22

<210> SEQ ID NO 17
<211> LENGTH: 22
<212> TYPE: DNA
<213> ORGANISM: Artificial Sequence
<220> FEATURE:
<223> OTHER INFORMATION: NC nucleic acid probe

<400> SEQUENCE: 17
acgagcgtct gctggctcca ca                                              22

<210> SEQ ID NO 18
<211> LENGTH: 22
<212> TYPE: DNA
<213> ORGANISM: Artificial Sequence
<220> FEATURE:
<223> OTHER INFORMATION: CP nucleic acid probe

<400> SEQUENCE: 18
acaaactcca aaacttcttc ca                                              22

<210> SEQ ID NO 19
<211> LENGTH: 22
<212> TYPE: DNA
<213> ORGANISM: Artificial Sequence
<220> FEATURE:
<223> OTHER INFORMATION: PL nucleic acid probe

<400> SEQUENCE: 19
atcagctagg caggtttaga ag                                              22

<210> SEQ ID NO 20
<211> LENGTH: 22
<212> TYPE: DNA
<213> ORGANISM: Artificial Sequence
<220> FEATURE:
<223> OTHER INFORMATION: CR nucleic acid probe

<400> SEQUENCE: 20
agttaagctt gttacagact ca                                              22
```

```
<210> SEQ ID NO 21
<211> LENGTH: 22
<212> TYPE: DNA
<213> ORGANISM: Artificial Sequence
<220> FEATURE:
<223> OTHER INFORMATION: CT nucleic acid probe

<400> SEQUENCE: 21
aacgcttatt ttgctagtgg cc                                              22

<210> SEQ ID NO 22
<211> LENGTH: 22
<212> TYPE: DNA
<213> ORGANISM: Artificial Sequence
<220> FEATURE:
<223> OTHER INFORMATION: CU2 nucleic acid probe

<400> SEQUENCE: 22
actcgttatt ttccagacag ac                                              22

<210> SEQ ID NO 23
<211> LENGTH: 22
<212> TYPE: DNA
<213> ORGANISM: Artificial Sequence
<220> FEATURE:
<223> OTHER INFORMATION: VS nucleic acid probe

<400> SEQUENCE: 23
ctaccaaaac gcttgtgcag tc                                              22

<210> SEQ ID NO 24
<211> LENGTH: 22
<212> TYPE: DNA
<213> ORGANISM: Artificial Sequence
<220> FEATURE:
<223> OTHER INFORMATION: CZ nucleic acid probe

<400> SEQUENCE: 24
tcgttgacca gtatagtatt tg                                              22

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
tccgtaggtg aacctgcgg                                                  19

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gctgcgttct tcatcgatgc                                                 20

<210> SEQ ID NO 27
<211> LENGTH: 29
<212> TYPE: DNA
<213> ORGANISM: Candida albicans

<400> SEQUENCE: 27
aaacattgct tgcggcggta acgtccacc                                       29
```

```
<210> SEQ ID NO 28
<211> LENGTH: 30
<212> TYPE: DNA
<213> ORGANISM: Candida dubliniensis

<400> SEQUENCE: 28
aacattgcta aggcggtctc tggcgtcgcc                                          30
```

COMPOSITIONS AND METHODS FOR THE DETECTION OF *CANDIDA* SPECIES

CROSS REFERENCE TO RELATED APPLICATION

This is a §371 U.S. National Stage of International Application No. PCT/US2006/037640, filed Sep. 26, 2006, which was published in English under PCT Article 21(2), which in turn claims the benefit of U.S. Provisional Application No. 60/721,419, filed Sep. 27, 2005, which is incorporated herein by reference in its entirety.

STATEMENT OF GOVERNMENT SUPPORT

This invention was made by The National Center for Infectious Diseases, Division of Bacterial and Mycotic Diseases, Centers for Disease Control and Prevention, an agency of the United States Government.

FIELD OF THE DISCLOSURE

This invention relates to compositions and methods for the detection and identification of species of *Candida* and, in particular, to nucleic acid probes that specifically hybridize to the internal transcribed spacer 2 (ITS2) of the ribosomal DNA (rDNA) repeat region of *Candida* species (such as *C. albicans* and *C. dubliniensis*).

BACKGROUND

Rapid identification of *Candida* isolates to the species level in the clinical laboratory has become more important because the incidence of candidiasis continues to rise in proportion to a growing number of patients at risk for infection with *Candida albicans* and, recently, with innately azole-resistant non-*albicans Candida* species (Fridkin and Jarvis, *Clin. Microbiol. Rev.*, 9:499-511, 1996; Jarvis, *Clin. Infect. Dis.*, 20:1526-1530, 1995; Wingard, *Clin. Infect. Dis.*, 20:115-125, 1995). This patient population has increased as a result of more intensive regimens of cancer therapy, complications of abdominal or cardiothoracic surgery, organ transplantations, burns, and trauma. Affected patients may be immunocompromised or not, and common risk factors include prolonged broad-spectrum antibiotic therapy, invasive devices such as indwelling Hickman catheters, and/or prolonged hospital stays (Fridkin and Jarvis, *Clin. Miciobiol. Rev.*, 9:499-511, 1996; Jarvis, *Clin. Infect. Dis.*, 20:1526-1530, 1995; Wenzel, *Clin. Infect. Dis.*, 20:1531-1534, 1995). Under these conditions, an antibiotic-resistant replacement flora, including *Candida* species, can proliferate in the gut and invade deep tissues from mucosal foci. This is especially true when mucosal integrity has been disrupted as a result of chemotherapy or surgery. In addition, as the number of risk factors increases, the odds of developing candidiasis multiply (Wenzel, *Clin. Infect. Dis.*, 20:1531-1534, 1995). Consequently, rapid identification to the species level is necessary for more timely, targeted, and effective antifungal therapy and to facilitate hospital infection control measures.

Identification of *Candida* species by conventional morphology and assimilation tests can be time consuming and laborious, especially for difficult-to-grow or morphologically atypical species (Warren and Hazen, "Cryptococcus and other yeasts of medical importance," In: *Manual of Clinical Microbiology*, 6th Edition, ed. by Murray et al., Washington, D.C.: American Society for Microbiology, 1995, pp. 723-737). Therefore, reliable, reproducible tests for the rapid identification of *Candida* isolates to the species level would be clinically and epidemiologically important.

Molecular methods for identification of *Candida* sp. have been developed. Some methods of molecular identification of fungi also can be very difficult or cumbersome to perform or require expensive, specialized equipment (e.g., Sandhu et al., *J. Clin. Microbiol.*, 35:1894-1896, 1997; Sandhu et al., *J. Clin. Microbiol.*, 33:2913-2919, 1995; Turenne et al., *J. Clin. Microbiol.*, 37:1846-1851, 1999). For instance, DNA sequencing, determination of sequence length polymorphisms, single-stranded conformational polymorphism analysis and restriction fragment length polymorphism analysis of PCR products amplified from fungal DNA are each quite laborious.

Nucleic acid probes specific for particular *Candida* species have been developed (e.g., Elie et al., *J. Clin. Microbiol.*, 36:3260-32655, 1998). Such probes have facilitated the development of methods for the rapid detection and identification of *Candida* species. For example, universal fungal primers can be used to amplify multicopy gene targets (such as the ITS2 region of the ribosomal DNA (rDNA) repeat region) from genomic DNA of *Candida* sp. present in a sample; then, amplicons can be detected using species-specific probes (e.g., Fujita et al., *J. Clin. Microbiol.*, 33:962-967, 1995; Shin et al., *J. Clin. Microbiol.*, 35:1454-1459, 1997; Shin et al., *J. Clin. Microbiol.*, 37:165-170, 1999). DNA probes have been designed to specifically detect a variety of *Candida* species, including *C. albicans*, *C. glabrata*, *C. guilliermondii*, *C. kefyr*, *C. krusei*, *C. lambica*, *C. lusitaniae*, *C. parapsilosis*, *C. pelliculosa*, *C. rugosa*, *C. tropicalis*, *C. zeylanoides*, *C. haemulonii*, *C. norvegensis*, *C. norvegica*, *C. utilis*, *C. viswanathii*, and *C. dubliniensis* (e.g., Elie et al., *J. Clin. Microbiol.*, 36:3260-32655, 1998).

Various methods of detecting the specific binding of *Candida*-specific probes to amplified target DNAs also have developed, including enzyme immunoassay (Elie et al., *J. Clin. Microbiol.*, 36:3260-32655, 1998), and exonuclease cleavage of fluorescent reporter dyes from labeled-probes (Shin et al., *J. Clin. Microbiol.*, 37:165-170). New technologies that can simultaneously detect large numbers of target nucleic acid sequences in a mixed sample (such as the multi-analyte profiling (MAP) system) have been and continue to be developed. Certain of such technologies can facilitate, for example, the high-throughput detection and classification of fungal pathogens in samples that may contain one or more such fungi. To implement this (and other more traditional) technologies, fungus-specific probes that distinguish among closely related fungi (such as species of *Candida*) are needed.

SUMMARY OF THE DISCLOSURE

This disclosure provides nucleic acid molecules (such as primers or probes) capable of distinguishing among particular species of *Candida*. In particular examples, nucleic acid probes specific for *Candida albicans* and *Candida dubliniensis* are provided. Disclosed nucleic acid probes provide unexpectedly high signal-to-background ratio when compared to other probes having similar specificity.

The provision of the disclosed nucleic acid molecules enables related methods, including, for example, methods of detection and/or differentiation of *Candida* sp., such as multi-analyte profiling (wherein multiple fungi can be simultaneously detected and identified in a single sample).

The foregoing and other features and advantages will become more apparent from the following detailed description of several embodiments, which proceeds with reference to the accompanying figures.

SEQUENCE LISTING

Figure 1:
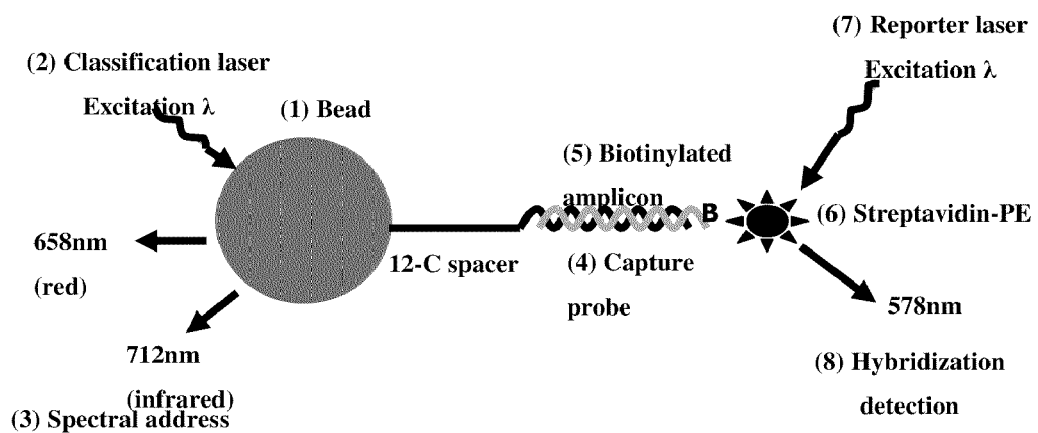
FIG. 1 shows a schematic representation of fluorescence signal generation and hybridization detection in one embodiment of the multi-analyte profiling (MAP) system.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows the nucleic acid sequence of *C. albicans*-specific probe, CA2.

SEQ ID NO: 2 shows the nucleic acid sequence of *C. dubliniensis*-specific probe, CD2.

SEQ ID NO: 3 shows the nucleic acid sequence of the ITS3 universal fungal forward primer.

SEQ ID NO: 4 shows the nucleic acid sequence of the ITS4 universal fungal reverse primer.

SEQ ID NO: 5 shows the nucleic acid sequence of *C. albicans*-specific probe, CA1.

SEQ ID NO: 6 shows the nucleic acid sequence of *C. dubliniensis*-specific probe, CD1.

SEQ ID NO: 7 shows the nucleic acid sequence of *C. glabrata*-specific probe, CG.

SEQ ID NO: 8 shows the nucleic acid sequence of *C. glabrata*-specific probe, CGE.

SEQ ID NO: 9 shows the nucleic acid sequence of *C. guilliermondii*-specific probe, GU.

SEQ ID NO: 10 shows the nucleic acid sequence of *C. haemulonii*-specific probe, CH.

SEQ ID NO: 11 shows the nucleic acid sequence of *C. kefyr*-specific probe, KF.

SEQ ID NO: 12 shows the nucleic acid sequence of *C. krusei*-specific probe, CK.

SEQ ID NO: 13 shows the nucleic acid sequence of *C. lambica*-specific probe, LA2.

SEQ ID NO: 14 shows the nucleic acid sequence of *C. lambica*-specific probe, LA4.

SEQ ID NO: 15 shows the nucleic acid sequence of *C. lusitaniae*-specific probe, LU.

SEQ ID NO: 16 shows the nucleic acid sequence of *C. norvegensis*-specific probe, NS.

SEQ ID NO: 17 shows the nucleic acid sequence of *C. norvegica*-specific probe, NC.

SEQ ID NO: 18 shows the nucleic acid sequence of *C. parapsilosis*-specific probe, CP.

SEQ ID NO: 19 shows the nucleic acid sequence of *C. pelliculosa*-specific probe, PL.

SEQ ID NO: 20 shows the nucleic acid sequence of *C. rugosa*-specific probe, CR.

SEQ ID NO: 21 shows the nucleic acid sequence of *C. tropicalis*-specific probe, CT.

SEQ ID NO: 22 shows the nucleic acid sequence of *C. utilis*-specific probe, CU2.

SEQ ID NO: 23 shows the nucleic acid sequence of *C. viswanathii*-specific probe, VS.

SEQ ID NO: 24 shows the nucleic acid sequence of *C. zeylanoides*-reactive probe, CZ.

SEQ ID NO: 25 shows the nucleic acid sequence of the ITS1 universal fungal forward primer.

SEQ ID NO: 26 shows the nucleic acid sequence of the ITS2 universal fungal reverse primer.

SEQ ID NO: 27 shows the nucleic acid sequence of a portion of the *C. albicans* ITS2 region of the rDNA gene repeat.

SEQ ID NO: 28 shows the nucleic acid sequence of a portion of the *C. dubliniensis* ITS2 region of the rDNA gene repeat.

DETAILED DESCRIPTION

I. Introduction

Disclosed herein are *Candida* sp.-specific nucleic acid sequences, which are useful for (among other things) detecting *Candida* sp., *Candida albicans*, and/or *Candida dubliniensis*. When used as probes for the presence of *Candida* sp. (for example, *Candida albicans*, and/or *Candida dubliniensis*) in a sample, the disclosed *Candida* sp.-specific nucleic acid sequences provide unexpectedly high signal-to-background ratio when compared to other probes having similar specificity.

In one embodiment, *Candida* sp.-specific nucleic acid sequence is an isolated nucleic acid molecule consisting of a nucleic acid sequence as set forth in SEQ ID NO: 1 or 2. Such nucleic acid molecule, in some examples, can be directly or indirectly immobilized on a solid support (such as a bead).

Other embodiments include a nucleic acid molecule consisting of a nucleic acid sequence as set forth in SEQ ID NO: 1 or 2, and heterologous molecule. In some such embodiments, the nucleic acid molecule and the heterologous molecule form a complex. A heterologous molecule can be, for example, a hapten (such as biotin or digoxigenin, or a combination thereof), a label (such as a fluorescent reporter dye, or enzyme, or a combination thereof), a linker (such as a hydrocarbon linker, in some cases from 6 to 18 carbons in length), a peptide, or a heterologous nucleic acid molecule, or a combination thereof. In some embodiments involving a fluorescent reporter dye, the fluorescent reporter dye is 6-carboxy-fluorescein, tetrachloro-6-carboxy-fluorescein, hexachloro-6-carboxy-fluorescein, or a combination thereof.

Also disclosed herein are methods of detecting *Candida albicans*. Method steps include detecting the specific hybridization of a probe having SEQ ID NO: 1 to a nucleic acid sequence in a sample, wherein the specific hybridization of the probe to the nucleic acid sequence detects the presence of *Candida albicans* in the sample. Other methods involve the detection of *Candida dubliniensis* by detecting the specific hybridization of a probe having SEQ ID NO: 2 to a nucleic acid sequence in a sample, wherein the specific hybridization of the probe to the nucleic acid sequence detects the presence of *Candida dubliniensis* in the sample. In some examples of either method, an additional step can involve amplifying an ITS2 nucleic acid sequence from the nucleic acid molecule in the sample. In more particular embodiments, amplifying the nucleic acid sequence involves the polymerase chain reaction and a forward primer having a sequence consisting essentially of SEQ ID NO: 3 or 25, or a reverse primer having a sequence consisting essentially of SEQ ID NO: 4. It is contemplated that biological samples be used in some disclosed method; such samples include whole blood, blood serum, tears, a skin scrape, urine, sputum, cerebrospinal fluid, prostate fluid, pus, bone marrow aspirate, bronchoalveolar levage (BAL), saliva, lung biopsy, or liver biopsy, or a combination of any thereof.

Further disclosed are kits for detecting the presence of a *Candida* sp. in a sample. In one embodiment a kit includes at least one probe consisting of a nucleic acid sequence as set forth in SEQ ID NOs: 1 and/or 2; and instructions for hybridizing the probe to an internal transcribed spacer-2 (ITS2) nucleic acid sequence of a *Candida* sp. fungus within the biological sample. In other embodiments, a kit also includes a primer consisting essentially of SEQ ID NO: 3, SEQ ID NO: 4, or SEQ ID NO: 25. Some kits may be useful for detecting *C. albicans*, in which case the probe consists of a nucleic acid sequence as set forth in SEQ ID NO: 1. Other kits may be useful for detecting *C. dubliniensis*, in which case the probe consists of a nucleic acid sequence as set forth in SEQ ID NO: 2.

Arrays (such as microarrays) for screening a sample for the presence of, or contamination by, one or more fungi are also disclosed. Such arrays include a plurality of nucleic acid probes each specific for a portion of a genomic sequence of a fungus, wherein the plurality of probes comprises at least one probe consisting of a nucleic acid sequence as set forth in SEQ ID NOs: 1 and/or 2; and a substrate, wherein the plurality of probes are arrayed on the substrate. In some examples, the genomic sequence of the fungus is the internal transcribed spacer 2 (ITS2) region located between the 5.8S and 26S rDNA genes.

Another disclosed embodiment involves a bead having a characteristic fluorescence emission wavelength, to which bead is directly or indirectly attached at least one *Candida* sp.-specific probe consisting of a nucleic acid sequence as set forth in SEQ ID NOs: 1 and/or 2.

II. Abbreviations and Terms

CA *C. albicans*
CD *C. dubliniensi*
CG *C. glabrata*
CK *C. krusei*
CP *C. parapsilosis*
CT *C. tropicalis*
EDC N-(3-dimethylaminodipropyl)-N'-ethylcarbodiimide
MAP multi-analyte profiling
PE phycoerythrin
PCR-EIA polymerase chain reaction-enzyme immunoassay In order to facilitate review of the various embodiments of the invention, the following explanations of specific terms are provided:

Amplification: A process for increasing the amount of (and/or number of copies of) a particular nucleic acid sequence (e.g., a DNA or RNA molecule) in a sample. One exemplary amplification method is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by such techniques as electrophoresis, restriction endonuclease cleavage patterns, oligonucleotide hybridization or ligation, and/or nucleic acid sequencing.

Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320,308; gap filling ligase chain reaction amplification, as disclosed in U.S. Pat. No. 5,427,930; and NASBA™ RNA transcription-free amplification, as disclosed in U.S. Pat. No. 6,025,134.

Animal: A living multi-cellular vertebrate or invertebrate organism, a category that includes, for example, mammals and birds. The term mammal includes both human and non-human mammals. Similarly, the term "subject" includes both human and veterinary subjects.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA can be synthesized in the laboratory by reverse transcription from messenger RNA extracted from cells.

Complex: A structure having two or more (such as 2, 3 or 4, or from 2 to 5, from 2 to 4, or from 2 to 3) physically interconnected components. A "component" can be a molecule (such as a nucleic acid molecule consisting of a nucleic acid sequence as in SEQ ID NO: 1 or 2, or a heterologous molecule) or an object (such as a bead). The interconnection between components of a complex can be covalent or non-covalent (such as electrostatic). Preferably, the interconnection between components of a complex is stable, at least, in standard saline buffers (e.g., phosphate-buffered saline (PBS), Tris-buffered saline (TBS), HEPES-buffered saline, and as otherwise commonly known in the art) at approximately neutral pH (e.g., pH 5.0-8.5, pH 5.5-8.0, pH 6.0-7.5, pH 6.5-7.5, or pH 7.0-7.5) and at conventional working temperatures (e.g., −20° C. to 100° C., 0° C. to 65° C., 5° C. to 50° C., 10° C. to 40° C., 15° C. to 35° C., 20° C. to 30° C., or at about room temperature). Exemplary complexes include molecules joined together with or without linkers by covalent bonds (such as a labeled nucleic acid molecule, or a nucleic acid molecule conjugated to a hapten or other heterologous molecule), or one or more molecules affixed (either covalently or non-covalently) to a bead. A complex of molecules joined together by covalent bonds may also be referred to as a "molecular complex."

Degenerate variant: A "degenerate variant" of a probe or primer includes sequences that have altered nucleic acid sequences, but retain their ability to bind to the target sequences (and identify or amplify the fungal target) with sufficient specificity. In some particular examples, no more than about 1, 2, 5, or 10 nucleic acids are changed, or the probe or primer retains at least 80%, 85%, 90%, or 95% sequence identity to the original sequence. Degenerate variants also include probe or primer sequences to which additional sequence has been added, while still retaining the noted specificity of the probe or primer.

Fungus: Living, single-celled and multicellular organisms belonging to Kingdom Fungi. Most species are characterized by a lack of chlorophyll and presence of chitinous cell walls, and some fungi can be multinucleated. Representative, non-limiting examples of fungi include *Candida* species (such as *Candida albicans* and/or *Candida dubliniensis*).

Heterogeneous molecule: Any molecule (for example, peptide, protein, heterologous nucleic acid, small molecule, label, hapten, and/or linker) that is not a nucleic acid sequence comprising a sequence set forth in SEQ ID NO: 1 or 2. In some instances, a heterogeneous molecule is capable of forming a complex with a nucleic acid molecule consisting of a sequence as in SEQ ID NO: 1 or 2. Such a complex may involve covalent bonds or stable non-covalent interactions between the heterologous molecule and the indicated nucleic acid molecule.

Homolog: A nucleotide sequence that shares a common ancestor with another nucleotide sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6×SSC, 5×Denhardt's solution, 0.5% SDS and 100 μg sheared salmon testes DNA, followed by 15-30 minute sequential washes at 65° C. in 2×SSC, 0.5% SDS, followed by 1×SSC, 0.5% SDS and finally 0.2×SSC, 0.5% SDS.

Isolated: An "isolated" biological component (such as a polynucleotide, polypeptide, cell, or microorganism) has been purified away from other biological components in a mixed sample (such as a cell, cell culture, tissue extract, tissue biopsy, or other sample). For example, an "isolated" polypeptide or polynucleotide is a polypeptide or polynucleotide that has been separated from the other components of a cell in which the polypeptide or polynucleotide was present (such as an expression host cell for a recombinant polypeptide or polynucleotide).

The term "purified" refers to the removal of one or more extraneous components from a sample. For example, where recombinant polypeptides are expressed in host cells, the polypeptides are purified by, for example, the removal of host cell proteins thereby increasing the percent of recombinant polypeptides in the sample. Similarly, where a recombinant polynucleotide is present in host cells, the polynucleotide is purified by, for example, the removal of host cell polynucleotides thereby increasing the percent of recombinant polynucleotide in the sample. Isolated polypeptides or nucleic acid molecules, typically, comprise at least 50%, at least 60%, at least 70%, at least 80%, at least 90%, at least 95% or even over 99% (w/w or w/v) of a sample.

Polypeptides and nucleic acid molecules are isolated by methods commonly known in the art and as described herein. Purity of polypeptides or nucleic acid molecules may be determined by a number of well-known methods, such as polyacrylamide gel electrophoresis for polypeptides, or agarose gel electrophoresis for nucleic acid molecules.

Nucleic acid molecule: This term refers to a polymeric form of nucleotides, which may include both sense and antisense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

Oligonucleotide: A nucleic acid molecule generally comprising a length of 200 bases or fewer. The term often refers to single-stranded deoxyribonucleotides, but it can refer as well to single- or double-stranded ribonucleotides, RNA:DNA hybrids and double-stranded DNAs, among others. In some examples, oligonucleotides are 10 to 60 bases in length, such as about 12, 13, 14, 15, 16, 17, 18, 19 or 20 bases in length. Other exemplary oligonucleotides are about 25, 30, 35, 40, 45, 50, 55 or 60 bases in length. Oligonucleotides may be single-stranded, e.g., for use as probes or primers, or may be double-stranded, e.g., for use in the construction of a mutant gene. Oligonucleotides can be either sense or antisense with respect to a target nucleic acid sequence. An oligonucleotide can be derivatized or modified in any manner known in the art.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. Typically, chemically synthesized DNA oligonucleotides are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP. The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well-known, this reaction can be prevented selectively, where desired, by removing the 5' phosphates of the other polynucleotide(s) prior to ligation.

Operably linked: A first molecule, such as a nucleic acid or protein, is operably linked with a second molecule when the first molecule is placed in a functional relationship with the second molecule. For instance, a promoter is operably linked to a nucleic acid coding sequence if the promoter affects the transcription or expression of the coding sequence. Generally, operably linked nucleotide sequences are contiguous and, where necessary to join two protein-coding regions, in the same reading frame.

ORF (open reading frame): A series of nucleotide triplets (codons) coding for amino acids without any internal termination codons. These sequences are usually translatable into a peptide.

Probes and primers: A probe comprises an isolated nucleic acid capable of hybridizing to a template nucleic acid. In some instances, a detectable label or reporter molecule can be attached to a probe. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed in, for example, Sambrook et al. (*Molecular Cloning: A Laboratory Manual* (Cold Spring Harbor Laboratory Press, Cold Spring Harbor, N.Y., 2001)) and Ausubel et al., eds. (*Short Protocols in Molecular Biology* (John Wiley and Sons, New York, N.Y., 1999)).

Primers are short nucleic acid molecules, for example DNA oligonucleotides 15 nucleotides or more in length. Primers can be annealed to a complementary target DNA strand by nucleic acid hybridization to form a hybrid between the primer and the target DNA strand, and the primer can be extended along the target DNA strand by a DNA polymerase enzyme. Primer pairs can be used for amplification of a nucleic acid sequence, e.g., by the polymerase chain reaction (PCR) or other nucleic acid amplification methods.

Methods for preparing and using probes and primers are described, for example, in Sambrook et al.; Ausubel et al., eds.; and Innis et al. (*PCR Applications, Protocols for Functional Genomics* (Academic Press, Inc., San Diego, Calif., 1999)). PCR primer pairs can be derived from a known sequence, for example, by using computer programs intended for that purpose such as Primer3 (Whitehead Institute for Biomedical Research, Cambridge, Mass.; this program is accessible through the Whitehead Institute's website). The specificity of a particular probe or primer increases with its length.

A "species-specific" probe is a probe shown to be capable of differentiating a species of fungus from another species in the same genus (e.g., distinguishing between *C. albicans* and *C. dubliniensis*). A "microbe-specific" probe is a probe that is capable of differentiating one genus of fungi from another genus of fungi (e.g., distinguishing *Candida* sp. from *Histoplasma* sp., *Coccidioides* sp., or *Paracoccidioides* sp.). A species-specific probe can be a microbe-specific probe.

Specific binding: The particular interaction between a binding agent and its target. Such interaction is mediated by one or, typically, more noncovalent bonds between the binding agent and its target (or, often, between the binding agent and a specific region or portion of its target). In contrast to non-specific binding sites, specific binding sites are saturable. Accordingly, one exemplary way to characterize specific binding is by a specific binding curve. A specific binding curve shows, for example, the amount of binding agent bound to a fixed target amount as a function of binding agent concentration. As binding agent concentration increases under these conditions, the amount of bound binding agent will saturate.

Sample: A specimen or culture obtained from an animal, plant, or the environment. An "environmental sample" includes a sample obtained from inanimate objects or reservoirs within an indoor or outdoor environment. Environmental samples include, but are not limited to: soil, water, dust, and air samples; bulk samples, including building materials, furniture, and landfill contents; and other reservoir samples, such as animal refuse, harvested grains, and foodstuffs.

A "biological sample" is a sample obtained from a plant or animal subject. As used herein, biological samples include all clinical samples useful for detection of microbial or fungal infection in subjects, including, but not limited to, organs, tissues, cells, and/or bodily fluids. Exemplary biological samples include blood (such as blood derivatives and fractions of blood, e.g., serum), extracted galls, biopsied or surgically removed tissue (including tissues that are, for example, unfixed, frozen, fixed in formalin and/or embedded in paraffin), tears, milk, skin scrapes, surface washings, urine, sputum, cerebrospinal fluid, prostate fluid, pus, bone marrow aspirates, bronchoalveolar levage (BAL), saliva, liver biopsy, or lung biopsy or a combination of any thereof. In particular embodiments, the biological sample is obtained from an animal subject, such as a human.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.,* 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al., *J. Mol. Biol.* 215:403-410, 1990) is available from several sources, including the National Center for Biotechnology Information (NCBI, Bethesda, Md.) and on the internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 50%, at least 60%, at least 70%, at least 80%, at least 85%, at least 90%, or at least 95% sequence identity.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity.

Transformed: A transformed cell is a cell into which a nucleic acid has been introduced by molecular biology techniques. The term "transformation" encompasses all techniques by which a nucleic acid molecule might be introduced into such a cell, including transfection with viral vectors, transformation with plasmid vectors, and introduction of naked DNA by such techniques as electroporation, lipofection, and particle gun acceleration.

Vector: A nucleic acid molecule capable of transporting a non-vector nucleic acid sequence which has been introduced into the vector. One type of vector is a "plasmid," which refers to a circular double-stranded DNA into which non-plasmid DNA segments may be ligated. Other vectors include cosmids, bacterial artificial chromosomes (BAC) and yeast artificial chromosomes (YAC). Another type of vector is a viral vector, wherein additional DNA segments may be ligated into all or part of the viral genome. Certain vectors are capable of autonomous replication in a host cell into which they are introduced (for example, vectors having a bacterial origin of replication replicate in bacteria hosts). Other vectors can be integrated into the genome of a host cell upon introduction into the host cell and are replicated along with the host genome. Some vectors contain expression control sequences (such as promoters) and are capable of directing the transcription of an expressible nucleic acid sequence that has been introduced into the vector. Such vectors are referred to as "expression vectors." A vector can also include one or more selectable marker genes and/or genetic elements known in the art.

Unless otherwise explained, all technical and scientific terms used herein have the same meaning as commonly understood by one of ordinary skill in the art to which this invention belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8).

The singular terms "a," "an," and "the" include plural referents unless context clearly indicates otherwise. "Comprising" means "including." "Comprising A or B" means "including A or B" or "including A and B." It is further to be understood that all base sizes or amino acid sizes, and all molecular weight or molecular mass values, given for nucleic acids or polypeptides are approximate, and are provided for description.

All publications, patent applications, patents, and other references mentioned herein are incorporated by reference in their entirety to the extent permitted by applicable law. In case of conflict, the present specification, including explanations of terms, will control.

Suitable methods and materials for the practice or testing of the invention are described below. However, the provided materials, methods, and examples are illustrative only and are not intended to be limiting. Accordingly, except as otherwise noted, the methods and techniques of the present invention can be performed according to methods and materials similar or equivalent to those described and/or according to conventional methods well known in the art and as described in various general and more specific references that are cited and discussed throughout the present specification (see, e.g., Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and Supplements to 2000); Ausubel et al., *Short*

Protocols in *Molecular Biology: A Compendium of Methods from Current Protocols in Molecular Biology*, 4th ed., Wiley & Sons, 1999; and Harlow and Lane, *Antibodies: A Laboratory Manual*, Cold Spring Harbor Laboratory Press, 1990 and 1999).

III. *Candida* sp.-Specific Nucleic Acid Molecules

This disclosure provides particular nucleotide sequences from the ITS2 regions of the *C. albicans* or *C. dubliniensis* genome, which sequences can be used for *C. albicans-* or *C. dubliniensis*-specific probes or primers, respectively. Such *Candida* sp.-specific probes or primers are useful, for example, in methods for differentiating species of *Candida* (such as *C. albicans* and/or *C. dubliniensis*) from one another and from other environmentally, clinically or medically important fungi. When used as probes, for example, the disclosed sequences have a superior signal-to-background ratio as compared to previously described *C. albicans-* or *C. dubliniensis*-specific probes. Although not limited to a particular mechanism of action, such enhanced signal to background may result from superior reactivity of the disclosed probes with their respective DNA targets. Exemplary nucleic acid molecules include:

| Source | Sequence | |
|---|---|---|
| *C. albicans* | AT TGC TTG CGG CGG TAA CGT | (SEQ ID NO: 1) |
| *C. dubliniensis* | AA GGC GGT CTC TGG CGT CGC C | (SEQ ID NO: 2) |

In addition, the disclosure encompasses nucleic acid sequences (which as defined herein also includes the complementary sequence and corresponding RNA sequences) with at least 75% (for example at least 85%, at least 95% or at least 98%) sequence identity to the isolated ITS2 sequence from *C. albicans* (SEQ ID NO: 1) or *C. dubliniensis* (SEQ ID NO: 2), or degenerate variants of either thereof. Such derivative sequences can be used as probes or primers for the detection or amplification of target sequences.

Also disclosed are isolated oligonucleotides (which as defined herein also includes the complementary sequence and corresponding RNA sequences) including at least about 10 consecutive nucleotides, or at least about 12, at least about 15, or at least about 18 consecutive nucleotides, from the *Candida* ITS2 sequences disclosed herein (e.g., SEQ ID NO: 1 or 2). These oligonucleotides can be employed as effective DNA hybridization probes or primers useful for amplification. Such probes and primers are particularly useful in the detection and speciation of *Candida*.

In some embodiments, any of the probes or primers disclosed herein is also of a maximum length, for example no more than 15, 25, 25, 40, 50, 75, 100, or 150 nucleotides in length. Any of the isolated nucleic acid sequences disclosed herein may consist or consist essentially of the disclosed sequences, or comprise nucleic acid molecules that have a maximum length of 15, 20, 25, 30, 35, 40, 45, 50, 55, 60, 65, 70, 75 or 80 contiguous nucleotides of the disclosed sequence.

A heterologous molecule can be directly or indirectly affixed to a disclosed *Candida* sp.-specific nucleic acid molecule (e.g., a *C. albicans-* or *C. dubliniensis*-specific probe or primer, or a nucleic acid molecule consisting of the sequence set forth in SEQ ID NO: 1 or 2). A heterologous molecule can include any molecule that is not a nucleic acid molecule having a sequence that is naturally contiguous with the nucleic acid sequence of the *Candida* sp.-specific nucleic acid molecule. Thus, for example, a heterologous molecule can include a label, a linker, a hapten, a heterologous nucleic acid molecule, a peptide (such as an epitope tag), a protein (such as an enzyme, streptavidin, or avidin), or a combination thereof.

A heterologous molecule can be affixed to a disclosed *Candida* sp.-specific nucleic acid molecule at any convenient site in the *Candida* sp.-specific nucleic acid molecule. In particular examples, a heterologous molecule will be joined to a disclosed *Candida* sp.-specific nucleic acid molecule at either or both end (i.e., at the 5' and/or 3' end(s)).

A heterologous molecule can be affixed to a disclosed *Candida* sp.-specific nucleic acid molecule by any method known in the art. Affixation may be the result of covalent or non-covalent (such as electrostatic) interactions; such as between the heterologous nucleic acid molecule and a disclosed *Candida* sp.-specific nucleic acid molecule. Various chemical or molecular biological methods are commonly known for conjugating, fusing, attaching, covalently bonding, or otherwise attaching heterologous molecules to a *Candida* sp.-specific nucleic acid molecule. For example, Shin et al. (*J. Clin. Microbiol.*, 37:165-170, 1999) describe 3'- and 5'-end labeling of *Candida* sp.-specific probes with fluorescent or quencher dyes; Elie et al. (*J. Clin. Microbiol.*, 36:3260-3265, 1998) describe 5'-end labeling of *Candida* sp.-specific probes with digoxigenin or biotin; and Example 1 herein describes linker (e.g., a hydrocarbon linker) attachment to *Candida* sp.-specific probes.

A linker is a chemical arm between two reactants, for instance a *Candida* sp.-specific probe and a reactive group on a bead. To accomplish the requisite chemical structure, each of the reactants includes a reactive group (or is modified to include a reactive group). Representative combinations of such groups are amino with carboxyl to form amide linkages; carboxy with hydroxy to form ester linkages or amino with alkyl halides to form alkylamino linkages; thiols with thiols to form disulfides; or thiols with maleimides or alkylhalides to form thioethers. In most instances, a linker forms a stable covalent linkage between the reactants (e.g., the label to the analyte). Exemplary linkers include hydrocarbons from about 1 to about 20 carbons in lengths which, optionally, may include from about 1 to about 10 heteroatoms (NH, O, S). Linkers may be branched or straight chain.

A label is any molecule or composition bound to an analyte, analyte, analog or binding partner that is detectable by spectroscopic, photochemical, biochemical, immunochemical, electrical, optical or chemical means. Exemplary labels include radioactive isotopes, enzymes (such as alkaline phosphatase, glucose-6-phosphate dehydrogenase ("G6PDH") and horseradish peroxidase); haptens; dyes; fluorescent dyes (such as fluorescein, isothiocyanate, rhodamine compounds, phycoerythrin, phycocyanin, allophycocyanin, o-phthaldehyde, fluorescamine, 6-carboxy-fluorescein, tetrachloro-6-carboxy-fluorescein, hexachloro-6-carboxy-fluorescein); chemiluminescent agents (such as isoluminol); sensitizers; coenzymes; enzyme substrates; photosensitizers; particles such as latex or carbon particles; suspendable particles; metal sol; or crystallite; or a combination of any thereof. Suitable enzymes, coenzymes, fluorescers and chemiluminescers are disclosed in U.S. Pat. Nos. 4,275,149 and 4,318,980. Methods for labeling and guidance in the choice of labels appropriate for various purposes are discussed, e.g., in Sambrook et al., *Molecular Cloning: A Laboratory Manual*, CSHL, New York, 1989 and Ausubel et al., *Current Protocols in Molecular Biology*, Greene Publ. Assoc. and Wiley-Intersciences, 1998.

A hapten is a relatively small molecule that contains an antigenic determinant (epitope) that may bind to a specific antibody but which is not itself antigenic unless complexed with an antigenic carrier such as a protein or cell. Exemplary haptens include biotin, digoxigenin, or digoxin.

IV. Method of Detecting *Candida* sp.

The presence of *Candida* sp. (e.g., *C. albicans* and/or *C. dubliniensis*) within a sample can be detected using the *Candida* sp.-specific nucleic acid molecules (e.g., probe and primer sequences) described herein. Fungal DNA can be directly detected or amplified prior to detection, and identification of the fungi from which the DNA originated can be confirmed by species-specific (e.g., *C. albicans*- and/or *C. dubliniensis*-specific) oligonucleotide probes. The methods described herein can be used for any purpose where the detection of fungi (such as *Candida* sp.) is desirable, including diagnostic and prognostic applications, such as in laboratory and clinical settings.

Appropriate samples include any conventional environmental or biological samples, including clinical samples obtained from a human or veterinary subject, for instance blood or blood fractions (e.g., serum), sputum, saliva, oral washings, skin scrapes, biopsied tissue, BAL, cerebrospinal fluid, or prostate fluid. Standard techniques for acquisition of such samples are available (see, e.g. Schluger et al., *J. Exp. Med.*, 176:1327-1333, 1992; Bigby et al., *Am. Rev. Respir. Dis.*, 133:515-518, 1986; Kovacs et al., *New Engl. J. Med.*, 318:589-93, 1988; Ognibene et al., *Am. Rev. Respir. Dis.*, 129:929-932, 1984). Serum or other blood fractions can be prepared according to standard techniques; about 200 µL of serum is an appropriate amount for the extraction of DNA for use in amplification reactions (see, e.g., Schluger et al., *J. Exp. Med.*, 176:1327-1333, 1992; Ortona et al., *Mol. Cell Probes*, 10:187-1990, 1996). The sample can be used directly or can be processed, such as by adding solvents, preservatives, buffers, or other compounds or substances.

Once a sample has been obtained, DNA can be extracted using standard methods. For instance, rapid DNA preparation can be performed using a commercially available kit (e.g., the InstaGene Matrix, BioRad, Hercules, Calif.; the NucliSens isolation kit, Organon Teknika, Netherlands; the QIAGEN Tissue Kit, QIAGEN, Inc., Valencia, Calif.). The DNA preparation technique can be chosen to yield a nucleotide preparation that is accessible to and amenable to nucleic acid amplification. Particular DNA extraction and preparation methods include (without limitation) the method described in Example 1 below.

Fungal nucleotide sequences can be detected through the hybridization of an oligonucleotide probe to nucleic acid molecules extracted from a biological or environmental sample, including a clinical sample. The sequence of appropriate oligonucleotide probes will correspond to a region within one or more of the fungal nucleotide sequences disclosed herein. Standard techniques can be used to hybridize fungal oligonucleotide probes to target sequences, such as the techniques described in U.S. Pat. Nos. 5,631,132; 5,426,027; 5,635,353; and 5,645,992; and PCT publication WO 98/50584.

In some embodiments, the probe is detectably labeled in some fashion, either with an isotopic or non-isotopic label. In alternative embodiments, the target (template) nucleic acid is labeled. Non-isotopic labels can, for instance, comprise a fluorescent or luminescent molecule, or an enzyme, co-factor, enzyme substrate, or hapten. The probe is incubated with a single-stranded preparation of DNA, RNA, or a mixture of both, and hybridization determined after separation of double- and single-stranded molecules. Alternatively, probes can be incubated with a nucleotide preparation after it has been separated by size and/or charge and immobilized on an appropriate medium.

In some embodiments, target fungal nucleotide sequences in a sample are amplified prior to using a hybridization probe for detection. For instance, it can be advantageous to amplify part or all of the ITS2 sequence, and then detect the presence of the amplified sequence pool. Any nucleic acid amplification method can be used, including the polymerase chain reaction (PCR) amplification. In particular embodiments, the PCR-EIA method, which is described below in more detail, is used for the amplification and detection of *Candida* sp. (such as *C. albicans* and/or *C. dubliniensis*). In other examples, the multi-analyte profiling (MAP) system is used together with disclosed *Candida* sp.-specific probes to detect *Candida* sp. (such as *C. albicans* and/or *C. dubliniensis*).

Figure 6:
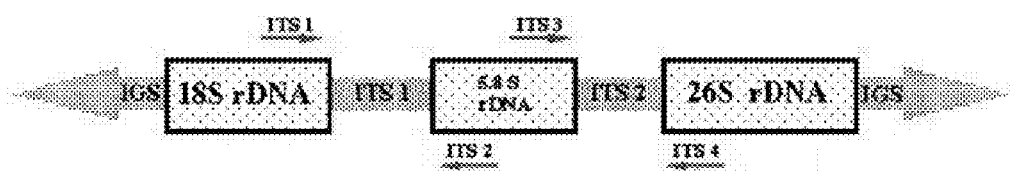
FIG. 6 is a diagram of fungal rDNA gene organization, including the hybridization sites of universal fungal primers, ITS1, ITS2, ITS3, and ITS4. The ITS2 region is shown between the 5.8S and 26S rDNA genes. The ITS2 region can be amplified, for example, using a combination of the ITS1 and IST4 primers and/or the ITS3 and ITS4 primers.

The sequential use of universal fungal primers for PCR amplification and species-specific probes can be used to identify *Candida* sp. (e.g., *C. albicans* and/or *C. dubliniensis*). Universal fungal primers, commonly called ITS1, ITS2, ITS3, and ITS4, allow amplification of a major portion of rDNA from most fungi, rather than that from only a single fungal species. A schematic of a fungal rDNA region is shown in FIG. 6. The internal transcribed spacer 2 (ITS2) sequence is located between the 5.8S and 28S coding sequences. Hybridization sites for the universal ITS1, ITS2, ITS3, and ITS4 primers are shown with arrows designating the direction of amplification (ITS1 and ITS3 are forward primers, and ITS2 and ITS4 are reverse primers).

The rDNA gene offers a suitable amplification target, not only because it contains binding sites for universal fungal primers, but also because the chromosome on which this gene is located contains approximately 100 gene copies that offer "pre-amplification" to increase amplicon yield and test sensitivity. Therefore, in some embodiments, the use of universal primers and a multiple copy gene target (rDNA) has greater utility and sensitivity for the identification of fungi in diverse samples than offered by gene targets of other embodiments.

PCR allows amplification and detection of small quantities of DNA, such as quantities of only a few nanograms, a few picograms, or less. The sensitivity of assays involving (or optionally involving) PCR, such as PCR-EIA or MAP, can be enhanced by various well-known modifications of the technique. For example, nested PCR utilizes a second set of primers, internal to the original set of primers, to re-amplify the target DNA using the amplicons from the first PCR as a template for the second PCR (see, e.g., Podzorski and Persing, In: *Manual of Clinical Microbiology*, 6th Edition, ed. by Murray et al., Washington, D.C.: ASM Press, 1995; Rappelli et al., *J. Clin. Microbiol.*, 36:3438-3440, 1998). Additionally, the PCR reaction can be continued through more cycles, continuing the geometric increase of DNA amplified, and alternative forms of Taq polymerase are available that have increased stability and accuracy throughout an increased number of PCR cycles. Commercially available Taq polymerases can be obtained from Roche Molecular Systems (Pleasanton, Calif.), Seikagaku America (Falmouth, Conn.), and other commercial suppliers.

While PCR-EIA offers one method of amplicon detection and identification of *Candida* sp. (e.g., *C. albicans* and/or *C. dubliniensis*), other methods of identification can be used. Amplicons can be produced using *Candida* sp.-specific primers and detected by electrophoresis in agarose gels and ethidium bromide staining (see, e.g., Aoki et al., *J. Clin. Microbiol.*, 37:315-320, 1999). The presence of a band in such an agarose gel is considered a positive result using specific primers. However, because different species of fungi can produce similar size amplicons, amplicon size detection can be supplemented with other identification methods.

Alternatively, the presence of a unique banding pattern after restriction enzyme digestion of fungal DNA, including DNA obtained by amplification, such as PCR, can be used for species identification, including methods commonly known as "genetic fingerprinting" based on restriction-fragment length polymorphism (RFLP) or randomly amplified polymorphic DNA (RAPD) analysis (see, e.g., Morace et al., *J. Clin. Microbiol.*, 35:667-672, 1997).

Species-specific probes (such as a nucleic acid molecule consisting of the sequence in SEQ ID NOs: 1 and/or 2) can be used to obtain a final identification of a *Candida* sp. using Southern blot, slot blot, dot blot, or another similar method (see, e.g., Sandhu et al., *J. Clin. Microbiol.*, 35:1894-1896, 1997; Sandhu et al., *J. Clin. Microbiol.*, 33:2913-2919, 1995; Tanaka et al., *J. Clin. Microbiol.*, 34:2826-2828, 1996). Additionally, an identification method using universal primers was developed by Turenne et al. (*J. Clin. Microbiol.*, 37:1846-1851, 1999), in which fungi are identified by the exact size of amplified DNA using an automated fluorescent capillary electrophoresis system.

The probes described herein not only provide a means to identify *Candida* sp. (e.g., *C. albicans* and/or *C. dubliniensis*) in culture, but also aid in the histological identification of such fungi in other samples, such as environmental and biological samples. Application of disclosed nucleic acid molecules (e.g., *C. albicans*- and/or *C. dubliniensis*-specific probes) to fungi in tissue sections can allow the differentiation of truly invasive organisms from simple colonizers, and multiple techniques can be employed to identify fungi in tissue using these probes. In some embodiments, fungal DNA is extracted from the tissue and identified by PCR-EIA or MAP. In other embodiments, the probes can be used for in situ hybridization, allowing localization of fungal DNA directly in the tissue. In still other embodiments, the combination of PCR and in situ hybridization procedures, where the target DNA is both amplified and hybridized in situ, can be employed. None of these methods should be considered mutually exclusive, however.

PCR-EIA

Figure 5:
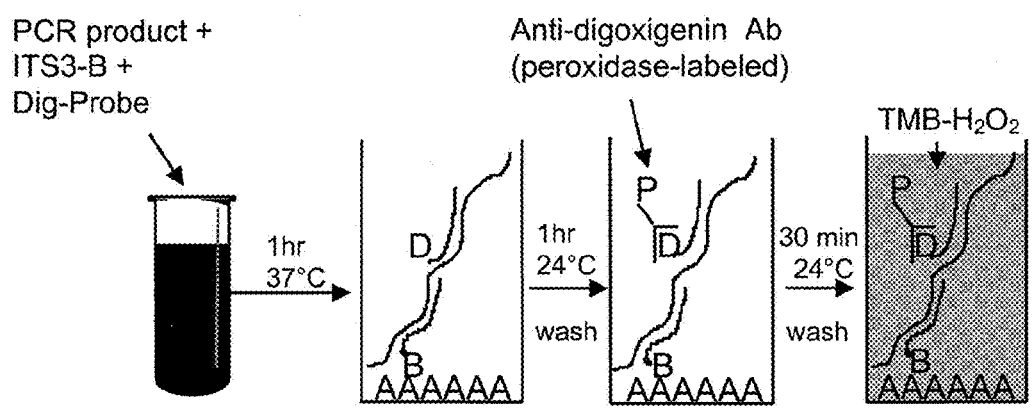
FIG. 5 illustrates a generalized polymerase chain reaction-enzyme immunoassay (PCR-EIA) method.

One non-limiting advantageous method for use of a disclosed *Candida* sp.-specific probe (for example, probes consisting of the nucleic acid sequence in SEQ ID NO: 1 or 2) is PCR-EIA. FIG. 5 illustrates a generalized PCR-EIA method. Briefly, denatured amplicons are hybridized with a biotin-labeled capture probe (B) and a digoxigenin-labeled detection probe (D) in an Eppendorf tube before addition to wells of a streptavidin-coated microtiter plate (A). Horseradish peroxidase-conjugated anti-digoxigenin antibody is then added, and amplicons bound to the wells are detected calorimetrically at $A_{650nm}$ after addition of TMB-$H_2O_2$ substrate. Conceivably, PCR-EIA can detect as little as a few fungal cells (e.g., *C. albicans* or *C. dubliniensis* DNA) present in a sample.

MAP System

Another non-limiting and advantageous method for use of disclosed *Candida* sp.-specific probes (for example, probes consisting of the nucleic acid sequence in SEQ ID NO: 1 or 2) is the MAP system. MAP technology permits the multiplexing of up to 100 different hybridization reactions in a single sample. In its conventional implementation, the system uses a liquid suspension array of 100 sets of 5.5 micron beads, each internally dyed with different ratios of two spectrally distinct fluorophores to assign it a unique spectral address. Each set of beads can be conjugated with a different capture molecule (such as a plurality of fungus-specific probes). The conjugated beads can then be mixed and incubated with sample in a microplate well to react with specific analytes. Following incubation with a fluorescently labeled reporter molecule, the contents of each microplate well are analyzed in a flow cytometry system, which aligns the beads in single file through a flow cell where two lasers excite the beads individually. The red classification laser excites the dyes in each bead, identifying its spectral address. The green reporter laser excites the reporter molecule associated with the bead, which allows quantification of the captured analyte. High-speed digital software record the fluorescent signals simultaneously for each bead, translating the signals into data for each bead-based assay. Each multiplex assay can use as little as 0.05 ng nucleic acid (such as genomic DNA) in a 12.5 to 25 µl sample.

One embodiment of MAP technology is shown schematically in FIG. 1. In this example, polystyrene beads (1), which are internally labeled with different ratios of red and infrared dyes, are excited by a classification laser (excitation wavelength=635 nm) (2) to reveal the unique spectral address (3) of each bead. Each bead has a covalently bound, species-specific oligonucleotide capture probe (4) attached to it that specifically binds in solution a biotinylated amplicon (5) of the complementary species. Streptavidin-phycoerythrin (PE) (6) binds to the biotin (B) label on the 5' end of the bead-coupled PCR amplicon. A reporter laser (7) excites the PE (excitation wavelength=532 nm) and a fluorescence signal (emission wavelength=578 nm) is detected, processed, and recorded by the MAP system (8). Other multiplexing detection methods are described, for example, in U.S. Pat. Nos. 6,838,243; 5,691,143; 5,470,710; 6,872,578; 6,280,618; and 6,277,641 and in U.S. Patent Application Publication Nos. 20050064452; 20030108913; and 20020012910.

In combination with the disclosed *Candida* sp.-specific probes and other previously described (or to-be-disclosed) fungus-specific probes, MAP technology can simultaneously detect and distinguish between up to 100 different fungi in one assay. In addition to the *Candida* sp.-specific probes described herein (e.g., probes having a sequence as in SEQ ID NO: 1 or 2), exemplary fungal species-specific DNA probes are available for *Candida albicans, Candida dubliniensis, Candida tropicalis, Candida glabrata, Candida guilliermondii, Candida krusei, Candida parapsilosis, C. haemulonii, Candida kefyr, Candida lambica, Candida lusitaniae, Candida norvegensis, Candida norvegica, Candida pelliculosa, Candida rugosa, Candida utilis, Candida viswanathii, Candida zeylanoides, Sporothrix schenckii, Cryptococcus neoformans, Pneumocystis carinii, Penicillium marneffei, Penicillium camembertii, Penicillium caseicolum, Penicillium chrysogenum, Penicillium glabrum, Penicillium griseofulvum, Penicillium italicum, Penicillium janthinellum, Penicillium purpurescens, Penicillium citrinum, Penicillium purpurogenum, Penicillium roquefortii, Penicillium rubefaciens, Penicillium spinulosum, Histoplasma capsulatum, Coccidioides immitis, Paracoccidioides brasiliensis, Aspergillus clavatus, Aspergillus granulosus, Aspergillus sydowii, Aspergillus flavipes, Aspergillus restrictus, Aspergillus versicolor, Aspergillus wentii, Aspergillus chevalieri, Aspergillus ustus, Aspergillus fumigatus, Aspergillus terreus, Aspergillus niger, Aspergillus nidulans, Aspergillus flavus, Blastomyces dermatitidis, Coccidioides posadasii, Pseudallescheria boydii, Rhizopus oryzae, Rhizomucor pusillus, Mucor circinelloides, Mucor indicus, Mucor racemosus, Sce-*

*dosporium prolificans*, and/or *Absidia corymbifera* (see, e.g., de Aguirre et al., *J. Clin. Microbiol.*, 42(8):3495-3504, 2004; Coignard et al., *J. Clin. Microbiol.*, 42(2):858-861, 2004; Ellepola et al., *Oral Microbiol. Immunol.*, 18(6):379-388, 2003; Lindsley et al., *J. Clin. Microbiol.*, 39(10):3505-3511, 2001; Shin et al., *J. Clin. Microbiol.*, 37(1):165-170, 1999; Elie et al., *J. Clin. Microbiol.*, 36(11):3260-3265, 1998; U.S. Pat. Nos. 6,372,430, 5,688,644, 5,645,992, 5,635,353, 5,631,132, and 5,426,027; U.S. Patent Publication No. 20030129600).

Like conventional microarray technologies (discussed below), the MAP system can be very sensitive and specific. In addition, the bead-based MAP system has several other advantages. First, the concentration of probes available for hybridization likely is higher than a microarray due to the three-dimensional surface of the beads (versus a two-dimensional surface of a microarray). This advantage may reduce reading difficulties, enhance exposure of components to reagents, and eliminate concentration gradients across the surface to which a component (such as a probe specific for a particular fungal species, like *C. albicans* and/or *C. dubliniensis*) is bound. In addition, the bead-based MAP system is relatively inexpensive, user friendly, simple in design, easy to perform, and data are automatically analyzed and calculated.

In a representative method employing MAP technology, a plurality of fungus-specific probes (e.g., at least *C. albicans* and/or *C. dubliniensis*-specific probes as set forth in SEQ ID NOs: 1 and 2, respectively) are independently attached to beads having a corresponding plurality of spectral characteristics. Thus, for instance, a *C. albicans*-specific probe (e.g., SEQ ID NO: 1) is attached to a first bead (or related first set of beads) having a first spectral emission wavelength specific for (or solely characteristic of) that particular first bead (or related first set of beads) and a *C. dubliniensis*-specific probe (e.g., SEQ ID NO: 2) is attached to a second bead (or related second set of beads) having a second spectral emission wavelength specific for (or solely characteristic of) that particular second bead (or related second set of beads) and so forth for as many probes as are of interest under a particular set of circumstances. In some embodiments, a plurality of probes for use with MAP technology includes two probes (e.g., a *C. albicans*-specific and a *C. dubliniensis*-specific probe, such as SEQ ID NOs: 1 and 2), or from two to 100, from two to 75, from two to 50, from two to 25, from 25 to 100, from 50 to 100, or from 75 to 100 fungal-specific probes. It is contemplated that at least one disclosed *C. albicans*-specific or *C. dubliniensis*-specific probe (such as SEQ ID NOs: 1 and/or 2) will be included in each plurality of MAP system probes.

The series of spectrally identifiable beads, each conjugated to a probe having specificity for a particular fungal species, is contacted with a sample. Samples useful in the disclosed methods have been discussed elsewhere. Such samples may contain nucleic acid molecules (e.g., genomic DNA of one or more fungi, or amplification products prepared from fungal genomic DNA or other relevant template nucleic acid) to which one or more of the plurality of fungal-specific probes will specifically bind. In particular examples, a sample will contain amplification products comprising nucleic acid sequences from the ITS2 region of fungal rDNA (such as *Candida* sp. ITS2 rDNA sequences). In other examples, the amplification products will include a label or other detectable tag, such as biotin or other hapten (see, e.g., FIG. 1). In some instances, the sample is pre-labeled with a nucleic-acid-specific dye. Exemplary dyes of this specificity are commonly known and are commercially available (e.g., ULYSIS Nucleic Acid Labeling Kits, ARES DNA Labeling Kits, and Alexa Fluor Oligonucleotide Amine Labeling Kits, each from Invitrogen).

The sample and the beads are contacted under conditions that permit the specific hybridization of nucleic acid molecules in the sample to the bead-immobilized probes. Particular hybridization conditions are discussed in Example 1 and elsewhere herein. The beads and unbound sample components are then separated, for instance, by centrifugation and, optionally, one or more wash steps. In some examples, the beads and bound sample components are labeled with a dye specific for the sample components. For example, where the sample includes amplification products having a tag (e.g., biotinylated amplification products), a dye conjugated to a binding partner that specifically binds the tag (e.g., avidin-dye or streptavidin-dye) can be used to specifically label the sample components bound to the beads. In each instance, sample components immobilized on the plurality of beads will have a collectively recognizable label (e.g., a distinctive fluorescence emission wavelength) and each spectrally identifiable bead will have its own recognizable characteristic (e.g., a distinctive fluorescence emission wavelength). In this way, each bead having a bound sample component can be easily and rapidly identified, for example, with commercially available equipment designed for this purpose (available from Luminex, MiraiBio, BioRad, Qiagen, and others).

V. Fungal Profiling Arrays

An array including a plurality of probes specific for particular fungal genera (e.g., *Candida* sp., *Sporothrix* sp., *Cryptococcus* sp., *Aspergillus* sp., *Pneumocystis* sp., *Penicillium* sp., *Fusarium* sp., *Mucor* sp., *Rhizopus* sp., *Histoplasma* sp., *Coccidioides* sp., and/or *Paracoccidioides* sp) and/or particular fungal species (e.g., *Candida* albicans, *Candida dubliniensis*, *Candida tropicalis*, *Candida glabrata*, *Candida guilliermondii*, *Candida krusei*, *Candida parapsilosis*, *C. haemulonii*, *Candida kefyr*, *Candida lambica*, *Candida lusitaniae*, *Candida norvegensis*, *Candida norvegica*, *Candida pelliculosa*, *Candida rugosa*, *Candida utilis*, *Candida viswanathii*, *Candida zeylanoides*, *Sporothrix schenckii*, *Cryptococcus neoformans*, *Pneumocystis carinii*, *Penicillium marneffei*, *Penicillium camembertii*, *Penicillium caseicolum*, *Penicillium chrysogenum*, *Penicillium glabrum*, *Penicillium griseofulvum*, *Penicillium italicum*, *Penicillium janthinellum*, *Penicillium purpurescens*, *Penicillium citrinum*, *Penicillium purpurogenum*, *Penicillium roquefortii*, *Penicillium rubefaciens*, *Penicillium spinulosum*, *Histoplasma capsulatum*, *Coccidioides immitis*, *Paracoccidioides brasiliensis*, *Aspergillus clavatus*, *Aspergillus granulosus*, *Aspergillus sydowii*, *Aspergillus flavipes*, *Aspergillus restrictus*, *Aspergillus versicolor*, *Aspergillus wentii*, *Aspergillus chevalieri*, *Aspergillus ustus*, *Aspergillus fumigatus*, *Aspergillus terreus*, *Aspergillus niger*, *Aspergillus nidulans*, *Aspergillus flavus*, *Blastomyces dermatitidis*, *Coccidioides posadasii*, *Pseudallescheria boydii*, *Rhizopus oryzae*, *Rhizomucor pusillus*, *Mucor circinelloides*, *Mucor indicus*, *Mucor racemosus*, *Scedosporium prolificans*, and/or *Absidia corymbifera*).

A fungal profiling array can be used, for instance, to screen a sample for the presence of one or more fungi having genomic nucleic acid sequences that specifically bind to the probes on the array. Such arrays can be used to rapidly detect and identify one or more fungi, for example a *Candida* fungus or a fungus of a particular genus and species, such as *C. albicans* or *C. dubliniensis*.

Arrays are arrangements of addressable locations on a substrate, with each address containing a nucleic acid, such as a probe. In some embodiments, each address corresponds to a single type or class of nucleic acid, such as a single probe, though a particular nucleic acid can be redundantly contained at multiple addresses. A "microarray" is a miniaturized array requiring microscopic or otherwise assisted examination for detection of hybridization. Larger "macroarrays" allow each address to be recognizable by the naked human eye and, in some embodiments, a hybridization signal is detectable without additional magnification. The addresses can be labeled, keyed to a separate guide, or otherwise identified by location.

In some embodiments, a fungal profile array is a collection of separate probes at the array addresses. As one, non-limiting example, an array includes probe(s) consisting of the nucleic acid sequences set forth in SEQ ID NOs: 1 and/or 2. The fungal profiling array is then contacted with a sample suspected of containing fungal nucleic acids under conditions allowing hybridization between the probe and nucleic acids in the sample to occur. Any sample potentially containing, or even suspected of containing, fungal nucleic acids can be used, including nucleic acid extracts, such as amplified or non-amplified DNA or RNA preparations. A hybridization signal from an individual address on the array indicates that the probe hybridizes to a nucleotide within the sample. This system permits the simultaneous analysis of a sample by plural probes and yields information identifying the fungal DNA or RNA contained within the sample. In alternative embodiments, the array contains fungal DNA or RNA and the array is contacted with a sample containing a probe. In any such embodiment, either the probe or the fungal DNA or RNA can be labeled to facilitate detection of hybridization.

The nucleic acids can be added to an array substrate in dry or liquid form. Other compounds or substances can be added to the array as well, such as buffers, stabilizers, reagents for detecting hybridization signal, emulsifying agents, or preservatives.

Within an array, each arrayed nucleic acid is addressable; that is, its location can be reliably and consistently determined within at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (e.g., in radially distributed lines, a "spokes and wheel" pattern, or ordered clusters).

An address within the array can be of any suitable shape and size. In some embodiments, the nucleic acids are suspended in a liquid medium and contained within square or rectangular wells on the array substrate. However, the nucleic acids can be contained in regions that are essentially triangular, oval, circular, or irregular. The overall shape of the array itself also can vary, though in some embodiments it is substantially flat and rectangular or square in shape.

Fungal profiling arrays can vary in structure, composition, and intended functionality, and can be based on either a macroarray or a microarray format, or a combination thereof. Such arrays can include, for example, at least 10, at least 25, at least 50, at least 100, or more addresses, usually with a single type of nucleic acid at each address. In the case of macroarrays, sophisticated equipment is usually not required to detect a hybridization signal on the array, though quantification can be assisted by standard scanning and/or quantification techniques and equipment. Thus, macroarray analysis can be carried out in most hospitals, agricultural and medial research laboratories, universities, or other institutions without the need for investment in specialized and expensive reading equipment.

Examples of substrates for the phage arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (e.g., glass or a supported membrane) or flexible (such as a polymer membrane). One commercially available product line suitable for probe arrays described herein is the Microlite line of Microtiter® plates available from Dynex Technologies UK (Middlesex, United Kingdom), such as the Microlite 1+96-well plate, or the 384 Microlite+384-well plate.

Addresses on the array should be discrete, in that hybridization signals from individual addresses should be distinguishable from signals of neighboring addresses, either by the naked eye (macroarrays) or by scanning or reading by a piece of equipment or with the assistance of a microscope (microarrays).

Addresses in a macroarray can be of a relatively large size, such as large enough to permit detection of a hybridization signal without the assistance of a microscope or other equipment. Thus, addresses of a macroarray can be as small as about 0.1 mm across, with a separation of about the same distance. Alternatively, addresses can be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses (i.e., larger addresses will usually be found on larger arrays, while smaller addresses can be found on smaller arrays). Such a correlation is not necessary, however.

The arrays herein can be described by their densities—the number of addresses in a certain specified surface area. For macroarrays, array density can be about one address per square decimeter (or one address in a 10 cm by 10 cm region of the array substrate) to about 50 addresses per square centimeter (50 targets within a 1 cm by 1 cm region of the substrate). For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the GeneChip® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques, similar to those used in the semiconductor industry. The masks are used to isolate chip exposure sites, and probes are chemically synthesized at these sites, with each probe in an identified location within the array. After fabrication, the array is ready for hybridization. The probe or the nucleic acid within the sample can be labeled, such as with a fluorescent label and, after hybridization, the hybridization signals can be detected and analyzed.

VI. Kits

The disclosed nucleic acid molecules (e.g., *C. albicans*- and *C. dubliniensis*-specific oligonucleotide primers and probes) can be supplied in the form of a kit for use in detection of fungi (such as *Candida* sp.), including kits for any of the arrays described above. In such a kit, an appropriate amount of one or more of oligonucleotide primers and/or probes (such as a primer or probe consisting of the sequence in SEQ ID NO: 1 or 2) is provided in one or more containers or held on a substrate. An oligonucleotide primer or probe can be provided, for instance, suspended in an aqueous solution or as a freeze-dried or lyophilized powder. The container(s) in which the oligonucleotide(s) are supplied can be any conventional container that is capable of holding the supplied form, for instance, microfuge tubes, ampules, or bottles. In some applications, pairs of primers can be provided in pre-measured single use amounts in individual, typically disposable, tubes or equivalent containers. With such an arrangement, the sample to be tested for the presence of fungal nucleic acids can be added to the individual tubes and amplification carried out directly.

The amount of each oligonucleotide primer supplied in the kit can be any appropriate amount, and can depend on the target market to which the product is directed. For instance, if the kit is adapted for research or clinical use, the amount of each oligonucleotide primer provided would likely be an amount sufficient to prime several PCR amplification reactions. A kit can include more than two primers in order to facilitate the PCR amplification of a larger number of fungal nucleotide sequences.

In some embodiments, kits can also include the reagents necessary to carry out PCR amplification reactions, including DNA sample preparation reagents, appropriate buffers (e.g., polymerase buffer), salts (e.g., magnesium chloride), and deoxyribonucleotides (dNTPs). One or more control sequences for use in the PCR reactions can also be supplied in the kit.

Kits can include either labeled or unlabeled oligonucleotide probes for use in detection of fungal (e.g., *Candida* sp.) nucleotide sequences. The appropriate sequences for such a probe will be any sequence that falls between the annealing sites of the two provided oligonucleotide primers, such that the sequence that the probe is complementary to is amplified during the PCR reaction. In some embodiments, the probe is complementary to a sequence within a *Candida* sp. (e.g., *C. albicans* or *C. dubliniensis*) rDNA ITS2 region.

One or more control sequences for use in the PCR reactions also can be supplied in the kit. Appropriate positive control sequences can be essentially as those discussed above. Particular embodiments include a kit for detecting and identifying a fungus based on the arrays described above. Such a kit includes at least two different probes (such as probes having the nucleic acid sequence in SEQ ID NO: 1 or 2) and instructions. A kit can contain more than two different probes, such as at least 10, at least 25, at least 50, at least 100, or more probes. The instructions can include directions for obtaining a sample, processing the sample, preparing the probes, and/or contacting each probe with an aliquot of the sample. In certain embodiments, the kit includes a device or apparatus for separating the different probes, such as individual containers (e.g., microtubules) or an array substrate (e.g., a 96-well or 384-well microtiter plate). In particular embodiments, the kit includes prepackaged probes, such as probes suspended in suitable medium in individual containers (e.g., individually sealed Eppendorf tubes) or the wells of an array substrate (e.g., a 96-well microtiter plate sealed with a protective plastic film). In other particular embodiments, the kit includes equipment, reagents, and instructions for extracting and/or purifying nucleotides from a sample.

In one embodiment, kits are supplied with instructions. In one specific, non-limiting example, the instructions are written instructions. In another such example, the instructions are contained in a videocassette or in a CD. The instructions may, for example, instruct the user how to use the primers to amplify the nucleic acid sequences, and then differentiate the species (and/or strains) of *Candida* using ITS2-specific probes disclosed herein. In one specific non-limiting example, the instructions direct the user to sequence the amplified nucleic acid to detect sequence differences indicative of the different *Candida* sp. Alternatively, probes may be used to detect the different sequences that are associated with each species or strain.

EXAMPLES

The following examples are provided to illustrate certain particular features and/or embodiments. These examples should not be construed to limit the invention to the particular features or embodiments described.

Example 1

Representative Materials and Methods

This Example describes materials and methods used in following Examples 2-5.

A. Microorganisms

Twenty-five strains of six different *Candida* species commonly isolated from patients with candidemia (Trick et al., *Clin. Infect. Dis.*, 35:627-630, 2002) were obtained from the Mycotic Diseases Branch Culture Collection, Centers for Disease Control and Prevention. The isolates used and their respective origins are listed in following Table 1:

TABLE 1

Source and characteristics of *Candida* species isolates used for probe testing

| Organism | Identification no.[a] | Source and/or characteristics |
|---|---|---|
| C. tropicalis | WO 745 | Unspecified |
| C. tropicalis | CDC 99-412 | Blood, Maryland |
| C. tropicalis | CDC 00-250 | Blood, Connecticut |
| C. tropicalis | ATCC 750 | Bronchomycosis |
| C. glabrata | CDC 99-283 | Blood, Connecticut |
| C. glabrata | CDC 99-377 | Blood, Connecticut |
| C. glabrata | CDC 99-508 | Blood, Connecticut |
| C. glabrata | CBS 861 | Mouth, The Netherlands |
| C. glabrata | CBS 860 | Urine, The Netherlands |
| C. dubliniensis | MF 663 | Vagina, New York |
| C. dubliniensis | CDC 00-127 | Blood, Connecticut |
| C. dubliniensis | CDC 98-200 | Blood, Maryland |
| C. aibicans | 32927 | Unspecified |
| C. albicans | CDC 99-63 | Blood, Connecticut |
| C. albicans | CDC 00-124 | Blood, Connecticut |
| C. albicans | CDC 00-125 | Blood, Connecticut |
| C. albicans | CDC 00-126 | Blood, Connecticut |
| C. krusei | ATCC 6258 | Sputum, Sri Lanka |
| C. krusei | CDC 259-75 | CDC Mycology Reference Laboratory |
| C. krusei | CDC 83 | CDC Mycology Reference Laboratory |
| C. parapsilosis | CDC 99-412 | Blood, Maryland |
| C. parapsilosis | CDC 99-519 | Blood, Connecticut |
| C. parapsilosis | CDC 00-109 | Blood, Connecticut |
| C. parapsilosis | CDC 00-128 | Blood, Connecticut |
| C. parapsilosis | CDC 00-460 | Blood, Connecticut |

[a]ATCC = American Type Culture Collection; CDC = Centers for Disease Control and Prevention; CBS = Centraalbureau voor Schimmelcultures Identification of the isolates was confirmed by API 20C AUX carbon assimilation testing (as described in Freydiere et al., *Med. Mycol.*, 39:9-33, 2001), growth characteristics on cornmeal Dalmau agar, and by polymerase chain reaction-enzyme immunoassay (PCR-EIA) (as described in Elie et al., *J. Clin. Miciobiol.*, 36:3260-3265, 1998).

B. Coupling of Probes to Microspheres (Beads)

Oligonucleotide probes for six medically important *Candida* species (*C. albicans, C. glabrata, C. tropicalis, C. parapsilosis, C. kausei* and *C. dubliniensis*) were synthesized as described previously (Elie et al., *J. Clin. Microbiol.*, 36:3260-3265, 1998) but rather than being digoxigenin end-labeled, each was labeled at the 5' end with an amino-modified 12-carbon spacer (as described by Diaz and Fell, *J. Clin. Microbiol.*, 42:3696-3706, 2004). This spacer was used for covalent attachment of the probes to the carboxylated beads using a carbodiimide coupling method described by Dunbar et al. (*J. Microbiol Meth.*, 53:245-252, 2003). The beads were differentially labeled so that those beads having the same attached probe could be identified. Previous studies using bead-based hybridization assays have employed a 12-C amino linker as in this Example (see, e.g., Diaz and Fell, *J. Clin. Microbiol.*, 42:3696-3706, 2004; Dunbar et al., *J. Microbiol. Meth.*, 53:245-252, 2003). Other studies have reported at least equivalent results using linkers from 6 to 18 carbons in length (Cowan et al., *J. Clin. Microbiol.*, 42:474-477, 2004; Wilson et al., *Mol. Cell. Probes*, 19:137-144, 2005). No significant differences in test sensitivity or specificity as a function of linker arm length were observed in the examples described herein.

Two hundred (200) pmol of an oligonucleotide probe and $2.5 \times 10^6$ microspheres (Luminex, Inc., Austin, Tex.) were mixed with 30 µg of fresh N-(3-dimethylaminodipropyl)-N'-ethylcarbodiimide (EDC; Pierce Chemicals, Rockford, Ill.) in 25 µl of 100 mM 2-(N-morpholino)-ethanesulfonic acid (MES), pH 4.5. The mixture was incubated in the dark for 30 minutes at 25° C. with constant shaking (140 rpm). The EDC treatment and incubation steps were then repeated and microspheres were washed with 1 ml of 0.1% SDS (Sigma Chemical Co., St. Louis, Mo.) followed by a second wash with 1 ml of 0.02% Tween 20 (Sigma). Coupled microspheres were then washed and suspended in 50 µl of TE buffer (0.01 M Tris-EDTA, pH 8.0). The process was repeated for each of the probes but with a differently labeled bead so that each of the probes were identifiable by the bead to which they were attached. Six bead sets were obtained in this manner and mixed by combining equal volumes (3 µl) of each together and the mixture was stored in the dark at 4° C. until used. Immediately before use, the mixture was brought up to a total volume of 1 ml in 1.5×TMAC buffer (1.5 M tetramethyl ammonium chloride, 75 mM Tris, 6 mM EDTA, and 0.15% sarkosyl, pH 8.0). Advantageously, the addition of 1.5 M tetramethyl ammonium chloride (TMAC) as the hybridization buffer helped to overcome any slight differences in melting temperatures among the probes. TMAC is believed to equalize AT and GC base pair stability (Diaz and Fell, *J. Clin. Microbiol.*, 42:3696-3706, 2004) and thereby decrease the influence of differences in the AT/GC ratios of probes which might otherwise promote selective hybridization of one probe over another.

C. PCR Amplification

The ITS2 region of *Candida* species rDNA was amplified using universal fungal primers ITS3 (forward primer; GCATCGATGAAGAACGCAGC (SEQ ID NO: 3)) and ITS4 (reverse primer; TCCTCCGCTTATTGATATGC (SEQ ID NO: 4)) as described by Elie et al. (*J. Clin. Microbiol.*, 36:3260-3265, 1998) except that (i) the reverse primer was biotinylated at the 5' end to allow binding of a streptavidin-R-phycoerythrin reporter dye, and (ii) an asymmetric PCR was conducted (i.e., ITS3 (5 µM stock) and ITS4 (20 µM stock) were used). Appropriate positive and negative controls were included and PCR contamination precautions were followed (see, e.g., Elie et al., *J. Clin. Microbiol.*, 36:3260-3265, 1998).

Using a four fold higher concentration of biotinylated reverse primer as compared to forward primer served a dual purpose: First, it increased the yield of single-stranded DNA produced during PCR amplification and thereby increased the efficiency of probe hybridization and, second, it further increased the amount of biotinylated reverse primer, compared to unbiotinylated forward primer, such that a higher amount of biotinylated amplicon was generated (thereby producing a higher hybridization signal). Asymmetric PCR has been used successfully in microarray assays and has been shown to increase the sensitivity of amplicon hybridization without affecting its specificity or reproducibility (Wei et al., *J. Biochem. Mol. Biol.*, 37:439-444, 2004).

D. Hybridization of Bead-Coupled Probes to PCR Amplicons

The bead mix was diluted in 1.5×TMAC hybridization buffer to a final concentration of 150 microspheres of each bead set per microliter. For the assay, 33 µl of this bead mix was added to 17 µl of target DNA (PCR amplicon) in a single well of a 96-well microtiter plate (Thermowell, VWR International, West Chester, Pa.). In instances where mixtures of DNA from different *Candida* species were to be tested in a single well of a microtiter plate, the total volume of target amplicon remained constant (17 µl) but volumes for individual species amplicons were reduced proportionately to maintain a 17 µl volume. The reaction mixture was then incubated in the thermal cycler for 5 minutes at 94° C. to denature the DNA and probes and amplicons were allowed to hybridize for an additional 30 minutes at 52° C. in the thermal cycler.

Detection of Hybridized Amplicons

Samples were removed from the thermal cycler and hybridized microspheres were pelleted by centrifugation at 2000×g for 3 minutes. The microspheres were then re-suspended in 75 µl of detection buffer (R-phycoerythrin-conjugated streptavidin (Molecular Probes, Eugene, Oreg.) diluted to 4 mg/ml in 1× hybridization buffer). Samples were incubated an additional 10 minutes at 52° C. in the thermal cycler and then analyzed in the MAP system flow cytometer (Bioplex; Bio-Rad Laboratories, Inc., Hercules, Calif.). Samples were analyzed in duplicate and positive and negative controls were included in each assay. Data for each well was acquired using the high speed signal processor included with the MAP system. Each bead was examined using two lasers: A classification laser (excitation wavelength=635 nm) to identify the unique spectral address of each bead and a reporter laser (excitation wavelength=532 nm) to measure the fluorescence produced by the R-phycoerythrin attached to the hybridized PCR product (as shown schematically in FIG. 1).

The digital signal processor and software included with the MAP system automatically calculated the median fluorescence intensity (MFI) for each bead set. A positive signal was defined as an MFI giving twice the background fluorescence intensity (BFI) for that bead-probe set. The BFI for a particular bead-probe set was calculated as the average of 12 reactions using water instead of template DNA in the PCR reaction. The sample-to-background (S/B) ratio was calculated for each test sample by dividing the mean MFI of three test runs by the mean BFI from the same three test runs.

E. Sensitivity Determination and the Detection of Mixed *Candida* Species

Serial dilutions of known concentrations of *Candida* species genomic DNA ($10^{-6}$ ng to 10 ng) were made before PCR amplification to determine the limit of test sensitivity of the MAP system. DNA was quantitated using a NanoDrop ND-1000 spectrophotometer (NanoDrop Technologies, Montchanin, Del.) according to the manufacturer's instructions. To determine if the MAP system could detect the presence of DNA from more than one *Candida* species simultaneously, target DNA from more than one *Candida* species was combined in a single well of a microtiter plate and tested as described above.

F. Statistical Analysis

Differences between the S/B ratios for each comparison group were analyzed using the two-tailed Student's t test, correlations between DNA concentration and S/B ratios were analyzed using the Pearson's r test, and groups were considered to be statistically different when the P value was <0.05.

Example 2

*C. albicans* and *C. dubliniensis* Probes Outperform Other Probes Specific for these Fungal Pathogens This Example demonstrates that disclosed *C. albicans* and *C. dubliniensis* probes provide surprisingly better signal-to-background (S/B) ratios than do currently available probes specific for these particular *Candida* species.

Previously, Elie et al. (*J. Clin. Microbiol.*, 36:3260-3265, 1998) created the following panel of probes specific for 18 *Candida* species for use in a PCR-EIA detection format:

| Probe | Sequence | SEQ ID NO. | Source |
|---|---|---|---|
| CA1 | AT TGC TTG CGG CGG TAA CGT CC | 5 | *C. albicans* |
| CD1 | AA GGC GGT CTC TGG CGT CGC CC | 6 | *C. dubliniensis* |
| CG | TA GGT TTT ACC AAC TCG GTG TT | 7 | *C. glabrata* |
| CGE | TT TAC CAA CTC GGT GTT GAT CT | 8 | *C. glabrata* |
| GU | CC CGG CCT TAC AAC AAC CAA AC | 9 | *C. guilliermondii* |
| CH | CC GTT GGT GGA TTT GTT TCT AA | 10 | *C. haemulonii* |
| KF | GA GAC TCA TAG GTG TCA TAA AG | 11 | *C. kefyr* |
| CK | GG CCC GAG CGA ACT AGA CTT TT | 12 | *C. krusei* |
| LA2 | AA AGC GAG GGG CCT TCT GCG CG | 13 | *C. lambica* |
| LA4 | GC GAG GGG CCT TCT GCG CGA AC | 14 | *C. lambica* |
| LU | CT CCG AAA TAT CAA CCG CGC TG | 15 | *C. lusitaniae* |
| NS | AC TGA GCG AAG TAC ACA ACA CT | 16 | *C. norvegensis* |
| NC | AC GAG CGT CTG CTG GCT CCA CA | 17 | *C. norvegica* |
| CP | AC AAA CTC CAA AAC TTC TTC CA | 18 | *C. parapsilosis* |
| PL | AT CAG CTA GGC AGG TTT AGA AG | 19 | *C. pelliculosa* |
| CR | AG TTA AGC TTG TTA CAG ACT CA | 20 | *C. rugosa* |
| CT | AA CGC TTA TTT TGC TAG TGG CC | 21 | *C. tropicalis* |
| CU2 | AC TCG TTA TTT TCC AGA CAG AC | 22 | *C. utilis* |
| VS | CT ACC AAA ACG CTT GTG CAG TC | 23 | *C. viswanathii* |
| CZ | TC GTT GAC CAG TAT AGT ATT TG | 24 | *C. zeylanoides* |

Recently, a technology has been developed for analysis of probe hybridization reactions in a flow cytometer. This method, the multi-analyte profiling (MAP) system, can rapidly detect up to 100 different probe hybridization reactions simultaneously in a single well of a microtiter plate. Probes CA1, CD1, CT, CGE, CK, or CP were tested in the MAP system against DNA from the respective *C. albicans*, *C. dubliniensis*, *C. tropicalis*, *C. glabrata*, *C. krusei*, or *C. parapsilosis* organisms listed in Table 1 (see Example 1). Each probe, directed to the internal transcribed spacer 2 (ITS2) region of ribosomal DNA (rDNA), was covalently linked to 1 of 100 fluorescently encoded microsphere (bead) sets. Each bead set was internally labeled with a different ratio of red to infrared fluorophores allowing each bead set to possess a unique spectral address. Biotinylated PCR amplicons were allowed to hybridize with bead sets coupled to specific probes and were then detected in the flow cytometer using a fluorescent reporter molecule (streptavidin-R-phycoerythrin). The signal intensities observed with the CA1 and CD2 probes in the detection of *C. albicans* and *C. dubliniensis*, respectively, were significantly less than that obtained for the CT, CGE, CK, or CP probes for the detection of the corresponding fungal pathogen.

It was determined that similar melting temperatures ($T_m$) would likely facilitate simultaneous detection of multiple *Candida* species with equivalent efficiency. Accordingly, the G+C content of the *C. albicans* and *C. dubliniensis* probes were adjusted by removing 2 (*C. albicans*) or 1 (*C. dubliniensis*) cytosine(s) (C) from the 3' end of each probe to produce the following modified probes:

| Probe | Sequence | SEQ ID NO. | Source |
|---|---|---|---|
| CA2 | AT TGC TTG CGG CGG TAA CGT | 1 | *C. albicans* |
| CD2 | AA GGC GGT CTC TGG CGT CGC C | 2 | *C. dubliniensis* |

In the modified panel of probes (including CA2, CD2, CT, CGE, CK, and CP), the probe length varied from 20 to 22 bp and the median G+C content was 55% (range=36 to 71%) to allow the final $T_m$ for all probes to be between 49° C. and 62° C.

Surprisingly, the relatively modest changes in CA2 and CD2 probe sequences resulted in unexpected increases in signal intensity. As shown in Table 2, CA2 was more than twice as effective as CA1 in detecting *C. albicans* (e.g., the mean MFI of the unmodified *C. albicans* probe (CA1) was 713 as compared to 1653 for the modified probe (CA2)). Similarly, CD2 was more than twice as effective as CD1 in detecting *C. dubliniensis* (e.g., the mean MFI of the unmodified *C. dubliniensis* probe (CD1) was 916 as compared to 2010 for the modified probe (CD2); see also, Table 2).

TABLE 2

CA2 and CD2 Provide Unexpectedly High Signal

| Name | Sequence | CA/CD[a] |
|---|---|---|
| CA[b] | AAACATTGCT TGCGG CGGTAA CGTCCACC | |
| CA1[d] | ATTGCTTGCGGCGGTAACGTCC | 713 |
| CA2 | ATTGCTTGCGGCGGTAACGT | 1653 |
| CD[c] | AACATTGCTAA GGCGG TCTCTGG CGTCGCC | |
| CD1 | AAGGCGGTCTCTGGCGTCGCCC | 916 |
| CD2 | AAGGCGGTCTCTGGCGTCGCC | 2010 |

[a]Median fluorescent intensity with PCR product from homologous DNA
[b]A portion of the *C. albicans* ITS2 region of the rDNA gene repeat (SEQ ID NO: 27). This portion is excerpted from a nucleic acid sequence alignment between GenBank Accession No. AJ249486 (*C. albicans* "18S rRNA (partial), 5.8S rRNA and 25S rRNA (partial) genes, internal transcribed spacer 1 (ITS1) and internal transcribed spacer 2 (ITS2)") and GenBank Accession No. AJ249485 (*C. dubliniensis* "18S rRNA (partial), 5.8S rRNA and 25S rRNA (partial) genes, internal transcribed spacer 1 (ITS1) and internal transcribed spacer 2 (ITS2)"). Spaces correspond to gaps introduced by the alignment software.
[c]A portion of the *C. dubliniensis* ITS2 region of the rDNA gene repeat (SEQ ID NO: 28). This portion is excerpted from a nucleic acid sequence alignment between GenBank Accession No. AJ249486 (*C. albicans* "18S rRNA (partial), 5.8S rRNA and 25S rRNA (partial) genes, internal transcribed spacer 1 (ITS1) and internal transcribed spacer 2 (ITS2)") and GenBank Accession No. AJ249485 (*C. dubliniensis* "18S rRNA (partial), 5.8S rRNA and 25S rRNA (partial) genes, internal transcribed spacer 1 (ITS1) and internal transcribed spacer 2 (ITS2)"). Spaces correspond to gaps introduced by the alignment software.
[d]Only the 5'end of each of the CA1, CA2, CD1, and CD2 probes (SEQ ID NOs: 5, 1, 6, and 2, respectively) is aligned with that portion of the corresponding ITS2 region.

Probe hybridization was also evaluated at different temperatures (37° C., 42° C., 45° C., and 52° C.) to determine temperature's effect on signal intensity in the MAP assay system. Some studies using similar methods have reported 52° C. or 55° C. to be a useful temperature for probe hybridization (Diaz and Fell, *J. Clin. Microbiol.*, 42:3696-3706, 2004; Cowan et al., *J. Clin. Microbiol.*, 42:474-477, 2004) whereas others reported hybridization to be equally successful at 37° C., 45° C., or 52° C. (Dunbar et al., *J. Microbiol. Meth.*, 53:245-252, 2003).

In this Example, the fluorescence signal intensity and stringency of hybridization was found to be highest at a hybridization temperature of 52° C. (e.g., mean S/B ratio±SE, n=3, for the *C. tropicalis* probe at 37° C., 2.7±0.8; at 42° C., 5.7:0.4; at 45° C., 5.2±1.9; and at 52° C., 32±1.6). Higher hybridization temperatures were not tested because the S/B ratios were as robust at 52° C. as those described in studies detecting other microorganisms (Diaz and Fell, *J. Clin. Microbiol.*, 42:3696-3706, 2004; Dunbar et al., *J. Microbiol, Meth.*, 53:245-252, 2003). The CA2 and CD2 probes exhibited similar hybridization temperature trends as the CA1 and CD1 probes, respectively.

Example 3

Identification and Differentiation of *Candida* Species

This Example demonstrates that CA2, CGE, CT, CP, CK, and CD2 specifically bind homologous DNA and do not significantly react with heterologous DNA.

The S/B ratio obtained for each species probe tested with its homologous DNA target was significantly greater than that obtained for probes tested against heterologous DNA targets as shown in Table 3.

TABLE 3

Specificity of probes used to detect *Candida* species DNA

| Target DNA (no.)[a] | Mean S/B ratio for indicated probe[b] | | | | | |
|---|---|---|---|---|---|---|
| | CA2 | CGE | CT | CP | CK | CD2 |
| *C. albicans* (5) | 58.7 ± 1.2 | 0[c] | 0 | 0 | 0 | 0 |
| *C. glabrata* (5) | 0 | 46.9 ± 2.1 | 0 | 0 | 0 | 0 |
| *C. tropicalis* (4) | 0 | 0 | 53.2 ± 3.8 | 0 | 0 | 0 |
| *C. parapsilosis* (5) | 0 | 0 | 0 | 59.9 ± 1.6 | 0 | 0 |
| *C. krusei* (3) | 0 | 0 | 0 | 0 | 54.7 ± 3.7 | 0 |
| *C. dubliniensis* (3) | 0 | 0 | 0 | 0 | 0 | 56.6 ± 1.9 |

[a]Number of isolates of each species tested in three separate experiments.

[b]The S/B (sample-to-background) ratio is generated by dividing the median fluorescence intensity of the test sample by the median fluorescence intensity for samples containing dH$_2$O instead of target DNA; the mean S/B ratio ± SE for the water blank was 1.0 ± 0.1 (n = 12).

[c]Mean S/B ratio ± SE for probes tested with heterologous *Candida* species DNA was 0.9 ± 0.03 (n = 25) (*C. albicans* probe, 0.75 ± 0.02; *C. glabrata* probe, 0.94 ± 0.09; *C. tropicalis* probe, 1.4 ± 0.17; *C. parapsilosis* probe, 0.98 ± 0.04; *C. krusei* probe, 0.97 ± 0.09; *C. dubliniensis* probe, 0.94 ± 0.06) and was represented as "0" in the table for ease of presentation. The S/B ratio using homologous probes was significantly higher than that using heterologous probes and for the water blank (P < 0.001).

The S/B ratio for all negative control samples, processed in the same manner as the test samples, but containing water instead of template DNA, was 1.0±0.1 (n=12). The mean S/B ratio for each probe was therefore approximately 58 times greater than the background fluorescence and the difference was statistically significant (P<0.001). No significant cross-reactivity was noted for any species probe tested against heterologous *Candida* species DNA (mean S/B ratio for all *Candida* species probes versus all heterologous *Candida* species DNA tested: 0.9±0.3, n=25, P<0.001, Table 3). S/B ratios were similar for all species probes tested except for the *C. tropicalis* and *C. glabrata* probes which gave somewhat lower signals despite the use of equal concentrations of target DNA (P<0.02; Table 3).

Example 4

Sensitivity of *Candida*-Specific Probes in the MAP System

This Example shows that *Candida*-specific probes (CA2, CGE, CT, CP, CK, and CD2) in the MAP system can detect as little as 5 pg homologous DNA.

To determine the limit of probe sensitivity, serial dilutions of genomic DNA were PCR-amplified and subsequently used in the MAP assay. The fluorescence signal was strongly positive for DNA concentrations ranging from 0.1 ng to 10 ng and the lower limit of DNA detection was 0.5 pg. Therefore, the MAP system for detecting the CA2, CGE, CT, CP, CK, or CD2 probe could detect DNA concentrations of 0.5 pg to 10 ng (highest DNA concentration tested) and the signal intensity correlated with the DNA concentration within this range (Pearson's r, P<0.05).

A sensitivity limit of 0.5 pg of genomic DNA (approximately 1 yeast cell per 4 µl sample) will likely be sufficient to detect all or most (95.1%) of the *Candida* species recovered from blood culture bottles (Shin et al., *J. Clin. Microbiol.*, 35:1454-1459, 1997).

Example 5

Detection of Target DNA within a Mixture of *Candida* Species Amplicons

This Example demonstrates that *Candida*-specific probes can simultaneously detect homologous DNA in a mixture of homologous and heterologous DNA targets contained within a single test well.

Figure 2:
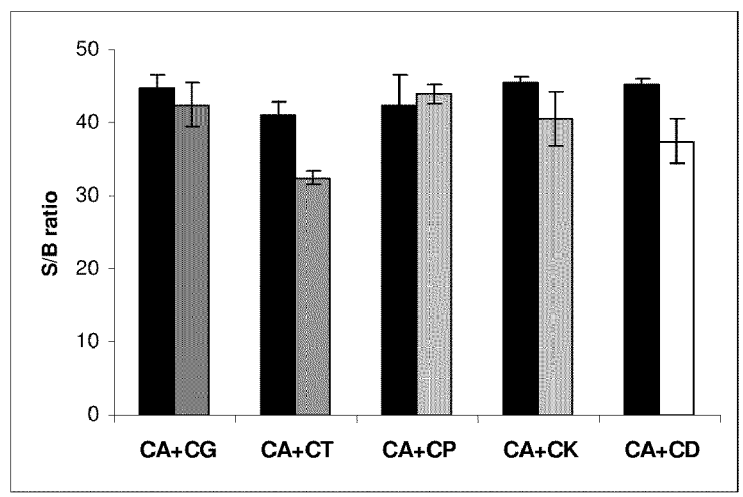
FIG. 2 is a bar graph showing detection, using the MAP system, of PCR amplicons from *C. albicans* mixed with those from other *Candida* species in equal proportions in each well. Similar results were noted when PCR amplicons from other species were mixed together and detected with homologous probes. CA=*C. albicans*; CG=*C. glabrata*; CP=*C. parapsilosis*; CT=*C. tropicalis*; CK=*C. krusei*; CD=*C. dubliniensis*.

PCR amplicons from two *Candida* species were mixed in equal (50:50, vol/vol) portions in each well of the microtiter plate and tested with their respective probe. The results shown in FIG. 2 demonstrate that the probes detected and differentiated each of the two *Candida* species present within the mixture. The signal intensities were found to be similar to those produced when each DNA was tested independently (P>0.05).

Figure 3:
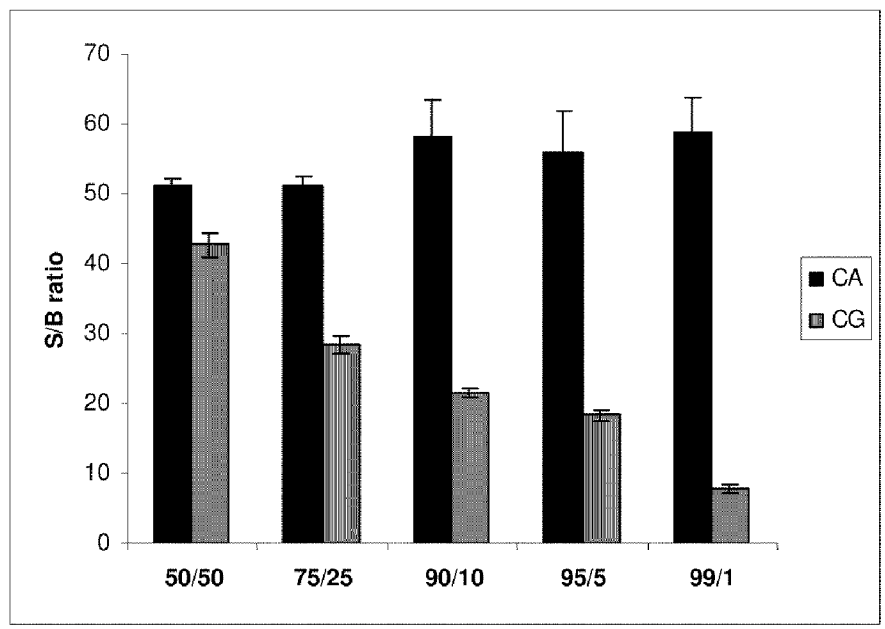
FIG. 3 is a bar graph showing S/B ratios obtained for the indicated proportions of PCR amplicons from *C. albicans* (CA) and *C. glabrata* (CG) mixed in the same well. The concentration of *C. albicans* amplicon was increased and the concentration of *C. glabrata* amplicon was decreased proportionally, keeping the reaction volume constant. There was a significant correlation between the DNA concentration and the S/B ratios for the two species tested (Pearson's r=0.95; P<0.001).

FIG. 3 illustrates the results of experiments wherein the volumes of *C. albicans* and *C. glabrata* DNA were varied such that as one increased, the other decreased. The signal intensity for the *C. glabrata* probe was concomitantly reduced, but was still detectable at a ratio of as little as one part to 99 parts. The fluorescence signal was therefore proportional to the concentration of DNA present for each species (Pearson's r, P<0.001) despite the presence of DNA from more than one *Candida* species.

Figure 4:
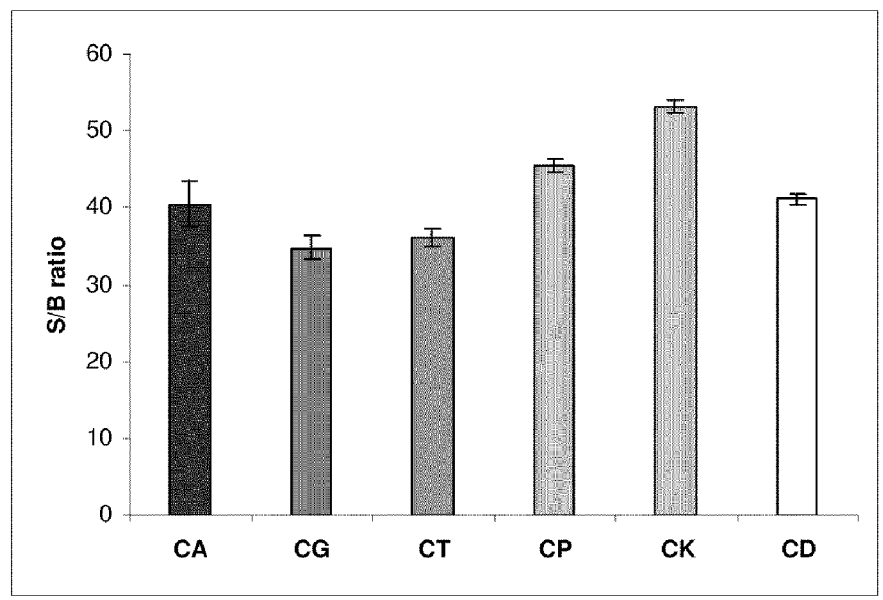
FIG. 4 is a bar graph showing the amplitude of the hybridization signals obtained using PCR amplicons from all 6 *Candida* species admixed in equal proportions in a single test well with all 6 *Candida* species probes. CA=*C. albicans*; CG=*C. glabrata*; CP=*C. parapsilosis*; CT=*C. tropicalis*; CK=*C. krusei*; CD=*C. dubliniensis*.

As shown in FIG. 4, each probe correctly identified its homologous species DNA when amplicons from all six *Candida* species were mixed together in a single well. Therefore, each *Candida* species DNA could be detected in the presence of all others. Also, no probe interfered with the detection of DNA by any of the other probes tested.

This Example demonstrates the use of species-specific probes to detect six species of *Candida* most commonly recovered from the blood in tertiary care hospitals (Trick et al., *Clin. Infect. Dis.*, 35:627-630, 2002). However, the number of probes that could be applied in this system may be increased to include those for other opportunistic pathogenic mycoses, or for many other *Candida* species, without modifying the test format. Furthermore, by using universal fungal primers to amplify the ITS2 region of rDNA common to all fungi, a single set of primers and amplification conditions could be used to amplify DNA from multiple fungi simultaneously. Because the MAP system can presently detect up to 100 DNA targets simultaneously, up to 100 different fungal pathogens could be processed in a single reaction. To date, as many as 45 MAP system probes have been used for simultaneous detection of human papilloma virus in a single well (Wallace et al., *J. Mol. Diagn.*, 7:72-80, 2005).

The disclosed *Candida*-specific probes as used in the MAP method allowed a *Candida* DNA-containing sample to be processed in less than one hour post-PCR amplification. Data for each well was acquired within 30 seconds, automatically converted to MFI values by the MAP system software, and presented on a spreadsheet for simple data analysis. In summary, this Example demonstrates a sensitive, specific, and rapid PCR-based, bead-probe fluid array system for the simultaneous detection of multiple *Candida* species.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. An isolated nucleic acid molecule consisting of the nucleic acid sequence as set forth in SEQ ID NO: 1 or 2.

2. The isolated nucleic acid molecule of claim 1 wherein the nucleic acid molecule is directly or indirectly immobilized on a solid support.

3. The isolated nucleic acid molecule of claim 2, wherein the solid support identifies the nucleic acid molecule that is immobilized on it.

4. The isolated nucleic acid molecule of claim 3, wherein the solid support is a bead having an identifiable characteristic.

5. A kit for detecting the presence of a *Candida* sp. in a sample, comprising:
   at least one probe consisting of the nucleic acid sequence as set forth in SEQ ID NOs: 1 and/or 2; and
   instructions for hybridizing the probe to an internal transcribed spacer-2 (ITS2) nucleic acid sequence of a *Candida* sp. fungus within the biological sample.

6. The kit of claim 5, further comprising a primer consisting essentially of SEQ ID NO: 3, SEQ ID NO: 4, or SEQ ID NO: 25.

7. The kit of claim 5, wherein the *Candida* sp. is *C. albicans* and the probe consists of the nucleic acid sequence as set forth in SEQ ID NO: 1.

8. The kit of claim 5, wherein the *Candida* sp. is *C. dubliniensis* and the probe consists of the nucleic acid sequence as set forth in SEQ ID NO: 2.

9. An array for screening a sample for the presence of or contamination by one or more fungi, comprising
   a plurality of nucleic acid probes each specific for a portion of a genomic sequence of a fungus, wherein the plurality of probes comprises at least one probe consisting of the nucleic acid sequence as set forth in SEQ ID NOs: 1 and/or 2; and
   a substrate, wherein the plurality of probes are arrayed on the substrate at addressable locations.

10. The array of claim 9, wherein the genomic sequence of the fungus is the internal transcribed spacer 2 (ITS2) region located between the 5.8S and 26S rDNA genes.

11. The array according to claim 9, wherein the array is a microarray.

12. A bead having a characteristic fluorescence emission wavelength, comprising at least one *Candida* sp.-specific probe consisting of the nucleic acid sequence as set forth in SEQ ID NOs: 1 and/or 2.

13. An isolated nucleic acid molecule consisting of the nucleic acid sequence as set forth in SEQ ID NO: 1 or 2, wherein the nucleic acid is labeled.

14. The nucleic acid molecule of claim 13, wherein the label is a fluorescent reporter dye, or enzyme, or a combination thereof.

15. The nucleic acid molecule of claim 14, wherein the fluorescent reporter dye is 6-carboxy-fluorescein, tetrachloro-6-carboxy-fluorescein, hexachloro-6-carboxy-fluorescein, or a combination thereof.

* * * * *